US010441646B2

(12) United States Patent
Eappen et al.

(10) Patent No.: US 10,441,646 B2
(45) Date of Patent: Oct. 15, 2019

(54) INFECTIOUS PLASMODIUM SPOROZOITES GROWN IN VITRO

(71) Applicant: SANARIA INC., Rockville, MD (US)

(72) Inventors: Abraham G. Eappen, Ellicott City, MD (US); Stephen L. Hoffman, Gaithersburg, MD (US)

(73) Assignee: Sanaria Inc., Rockville, MD (US)

( * ) Notice: Subject to any disclaimer, the term of this patent is extended or adjusted under 35 U.S.C. 154(b) by 0 days.

(21) Appl. No.: 15/858,574

(22) Filed: Dec. 29, 2017

(65) Prior Publication Data

US 2018/0161413 A1 Jun. 14, 2018

Related U.S. Application Data

(63) Continuation of application No. 15/095,360, filed on Apr. 11, 2016, now Pat. No. 9,878,026, which is a continuation of application No. PCT/US2015/028890, filed on May 1, 2015.

(60) Provisional application No. 62/016,981, filed on Jun. 25, 2014, provisional application No. 61/987,834, filed on May 2, 2014.

(51) Int. Cl.
*A61K 39/015* (2006.01)
*A61K 39/00* (2006.01)
*A61K 49/00* (2006.01)
*C12N 1/10* (2006.01)

(52) U.S. Cl.
CPC .............. *A61K 39/015* (2013.01); *C12N 1/10* (2013.01); *A61K 2039/52* (2013.01); *A61K 2039/522* (2013.01); *Y02A 50/412* (2018.01)

(58) Field of Classification Search
CPC ........................... A61K 39/015; A61K 39/002
USPC ................. 424/9.1, 9.2, 184.1, 269.1, 272.1; 435/243, 245, 258.1, 258.2
See application file for complete search history.

(56) References Cited

U.S. PATENT DOCUMENTS

| | | |
|---|---|---|
| 7,015,036 B2 | 3/2006 | Prachumsri et al. |
| 7,229,627 B2 | 6/2007 | Hoffman et al. |
| 8,043,625 B2 | 10/2011 | Sim et al. |
| 8,367,810 B2 | 2/2013 | Sim et al. |
| 8,802,919 B2 | 8/2014 | Hoffman et al. |
| 8,821,896 B2 | 9/2014 | Sim et al. |
| 8,992,944 B2 | 3/2015 | Sim et al. |
| 9,241,982 B2 | 1/2016 | Sim et al. |
| 9,278,125 B2 | 3/2016 | Chakravarty et al. |
| 9,616,115 B2 | 4/2017 | Sim et al. |
| 9,642,909 B2 | 5/2017 | Chakravarty et al. |
| 9,764,016 B2 | 9/2017 | Janse et al. |
| 2005/0208078 A1 | 9/2005 | Hoffman et al. |
| 2005/0220822 A1 | 10/2005 | Hoffman et al. |
| 2012/0156245 A1 | 6/2012 | Hoffman et al. |
| 2012/0288525 A1 | 11/2012 | Chakravarty et al. |
| 2013/0251750 A1 | 9/2013 | Sim et al. |
| 2015/0313980 A1 | 11/2015 | Janse et al. |
| 2016/0158351 A1 | 6/2016 | Chakravarty et al. |
| 2016/0175417 A1 | 6/2016 | Sim et al. |
| 2016/0216276 A1 | 7/2016 | Felgner et al. |
| 2016/0287688 A1 | 10/2016 | Eappen et al. |
| 2016/0320404 A1 | 11/2016 | Felgner et al. |
| 2017/0252419 A1 | 9/2017 | Janse et al. |
| 2017/0274061 A1 | 9/2017 | Sim et al. |

OTHER PUBLICATIONS

Schuster, Clinical Microbiology Reviews, vol. 15, No. 3, pp. 355-364, 2002.*
Abraham, E.G., et al., "Analysis of the *Plasmodium* and *Anopheles* transcriptional repertoire during ookinete development and midgut invasion," *J Biol Chem* 279(7):5573-5580, JBC Papers, United States (2004).
Adini, A. and Warburg, A., "Interaction of *Plasmodium gallinaceum* ookinetes and oocysts with extracellular matrix proteins," *Parasitology* 119(Pt 4):331-336, Cambridge University Press, United Kingdom (1999).
Agnandji, S.T., et al., "A Phase 3 Trial of RTS,S/AS01 Malaria Vaccine in African Infants," *The New England Journal of Medicine* 367(24):2284-2295, Massachusetts Medical Society, United States (2012).
Agnandji, S.T., et al., "First Results of Phase 3 Trial of RTS,S/AS01 Malaria Vaccine in African Children," *The New England Journal of Medicine* 365(20):1863-1875, Massachusetts Medical Society, United States (2011).
Al-Olayan, E.M., et al., "Complete Development of Mosquito Phases of the Malaria Parasite in Vitro," *Science* 295(5555):677-679, American Association for the Advancement of Science, United States (2002).
Alonso, P.L., et al., "A Research Agenda for Malaria Eradication: Vaccines," *PLoS Medicine* 8(1): e1000398:1-10, Public Library of Science, United States (2011).
Benedict, M.Q., et al., Methylparaben in *Anopheles gambiae* s.l. sugar meals increases longevity and malaria oocyst abundance but is not a preferred diet, *J Insect Physiol* 55(3):197-204, Elsevier Ltd., England (2009).
Benton, G., et al., "Advancing Science and Technology via 3D Culture on Basement Membrane Matrix," *Journal of Cellular Physiology* 221(1):18-25, Wiley-Liss, United States (2009).
Billker, O., "Calcium and a calcium-dependent protein kinase regulate gamete formation and mosquito transmission in a malaria parasite," *Cell* 117(4):503-514, Cell Press, United States (2004).
Boston Consulting Group on behalf of the Malaria Vaccine Initiative PATH, "Market Assessment for Malaria Vaccines, Jan. 2005," accessed at http://www.malariavaccine.org/sites/www.malariavaccine.org/files/content/resources/files/Market-Assessment-18Jan05-LB-BOS_000.pdf, accessed on Mar. 25, 2016, 167 pages.

(Continued)

*Primary Examiner* — Rodney P Swartz
(74) *Attorney, Agent, or Firm* — Sterne, Kessler, Goldstein & Fox P.L.L.C.

(57) ABSTRACT

The application is directed to in vitro-reared *Plasmodium* sporozoites of human host range wherein sporogony from gametocyte stage to sporozoite stage is external to mosquitoes, and methods of producing the same. Provided herein are in vitro-reared infectious *Plasmodium* sporozoites (SPZ) of human host range, particularly *P. falciparum, P. vivax, P. ovale, P. malariae*, and *P. knowlesi*, wherein sporogony from gametocyte stage to sporozoite stage is external to mosquitoes, and methods of producing the same.

18 Claims, 6 Drawing Sheets

(56) References Cited

OTHER PUBLICATIONS

Bounkeua, V., et al., "In vitro generation of *Plasmodium falciparum* ookinetes," *Am J Trop Med Hyg* 83 (6):1187-1194, The American Society of Tropical Medicine and Hygiene, United States (2010).

Chuang, I., et al., "DNA prime/Adenovirus boost malaria vaccine encoding *P. falciparum* CSP andAMA1 induces sterile protection associated with cell-mediated immunity," *PLoS One* 8(2):e55571:1-15, Public Library of Science, United States (2013).

Cullen, K.A. and Arguin, P.M., "Malaria Surveillance—United States, 2011," *Morbidity and Mortality Weekly Report Surveillance Summaries* 62(5):1-17, Epidemiology Program Office, Centers for Disease Control and Prevention, United States (2013).

Dessens, J.T., et al., "SOAP, a novel malaria ookinete protein involved in mosquito midgut invasion and oocyst development," *Mol Microbiol* 49(2):319-329, Blackwell Publishing Ltd., England (2003).

Garcia, C.R., et al., "Comparative cost models of a liquid nitrogen vapor phase (LNVP) cold chain-distributed cryopreserved malaria vaccine vs. a conventional vaccine," *Vaccine* 31(2):380-386, Elsevier Ltd, England (2012).

Hoffman, S.L., et al., "Development of a Metabolically Active, Non-Replicating Sporozoite Vaccine to Prevent *Plasmodium falciparum* Malaria," *Human Vaccines* 6(1):97-106, Landes Bioscience, United States (2010).

Hoffman, S.L., et al., "Protection of humans against malaria by immunization with radiation-attenuated *Plasmodium falciparum* sporozoites," *J Infect Dis* 185:1155-1164, Infectious Diseases Society of America, United States (2002).

Hughes, C.S., et al., "Matrigel: a Complex Protein Mixture Required for Optimal Growth of Cell Culture," *Proteomics* 10(9):11886-1890, Wiley-VCH, Germany (2010).

International Search Report and Written Opinion for International Application No. PCT/US2015/028890, ISA/US, Commissioner for Patents, Alexandria, Virginia, dated Jul. 16, 2015, 12 pages.

Kester, K.E., et al., "Randomized, Double-Blind, Phase 2a Trial of Falciparum Malaria Vaccines RTS,S/AS01B and RTS,S/AS02A in Malaria-Naive Adults: Safety, Efficacy, and Immunologic Associates of Protection," *The Journal of Infectious Diseases* 200(3):337-346, Infectious Diseases Society of America, United States (2009).

Klenow, P.J., "Learning Curves and the Cyclical Behavior of Manufacturing Industries," *Review of Economic Dynamics* 1:531-550, Academic Press, United States (1998).

Lieberman, M.B., "The learning curve and pricing in the chemical processing industries," *The RAND Journal of Economics* 15(2):213-228, The RAND Corporation, United States (1984).

Mali, S., et al., "Malaria Surveillance—United States, 2010," *Morbidity and Mortality Weekly Report Surveillance Summaries* 61(2):1-17, Epidemiology Program Office, Centers for Disease Control and Prevention, United States (2012).

March, S., et al., "A Microscale Human Liver Platform that Supports the Hepatic Stages of *Plasmodium falciparum* and *vivax*," *Cell Host Microbe* 14(1):104-115, Elsevier Inc., United States (2013).

Matuschewski, K., "Getting infectious: formation and maturation of *Plasmodium sporozoites* in the *Anopheles vector*," *Cellular Microbiology* 8(10):1547-1556, Blackwell Publishing Ltd., England (2006).

Mordmüller, B., et al., "Safety and immunogenicity of the malaria vaccine candidate GMZ2 in malaria-exposed, adult individuals from Lambaréné, Gabon," *Vaccine* 28(41):6698-6703, Elsevier B.V., Netherlands (2010).

Mutapi, F., et al., "Infection and Treatment Immunizations for Successful Parasite Vaccines," *Trends in Parasitology* 29(3):135-141, Elsevier Ltd., England (2013).

Olotu, A., et al., "Four-Year Efficacy of RTS,S/AS01E and its Interaction with Malaria Exposure," *The New England Journal of Medicine* 368(12):1111-1120, Massachusetts Medical Society, United States (2013).

Palacpac, N.M.Q., et al., "Phase Ib Randomized Trial and Follow-Up Study in Uganda of the Blood-Stage Malaria Vaccine Candidate BK-SE36," *PLoS One* 8(5):e64073:1-14, Public Library of Science, United States (2013).

Plowe, C.V., et al., "The Potential role of vaccines in the elimination of falciparum malaria and the eventual eradication of malaria," *J Infect Dis* 200:1646-1649, Infectious Disease Society of America, United States (2009).

Pradel, G., "Proteins of the Malaria Parasite Sexual Stages: Expression, Function and Potential for Transmission Blocking Strategies," *Parasitology* 134(Pt 14):1911-1929, Cambridge University Press, United Kingdom (2007).

Richie, T.L. and Saul, A., "Progress and challenges for malaria vaccines," *Nature* 415(6872):694-701, Macmillan Magazines Ltd., England (2002).

Roestenberg, M., et al., "Protection against a malaria challenge by sporozoite inoculation," *New England Journal of Medicine* 361(5):468-477, Massachusetts Medical Society, United States (2009).

Roestenberg, M., et al., "Controlled Human Malaria Infections by Intradermal Injection of Cryopreserved *Plasmodium falciparum* Sporozoites," *Am. J. Trop. Med. Hyg.* 88(1):5-13, The American Society of Tropical Medicine and Hygiene, United States (2013).

Sachs, J. and Malaney, P., "The Economic and Social Burden of Malaria," *Nature* 415(6872):680-685, Macmillan Magazines Ltd., England (2002).

Sack, B.K., et al., "Model for in vivo assessment of humoral protection against malaria sporozoite challenge by passive transfer of monoclonal antibodies and immune serum," *Infection and Immunity* 82(2):808-817, American Society for Microbiology, United States (2014).

Sattabongkot, J., et al., "Establishment of a Human Hepatocyte Line that Supports in Vitro Development of the Exo-Erythrocytic Stages of the Malaria Parasites *Plasmodium falciparum* and *P. Vivax*," *Am. J. Trop. Med. Hyg.* 74(5):708-715, The American Society of Tropical Medicine and Hygiene, United States (2006).

Savransky, T., et al., Development and Validation of an In Vitro, Cell-Free Method of Culturing Mosquito-Stage *Plasmodium falciparum*, Abstract #1446, *ASTMH* 91(5S):440, The American Society of Tropical Medicine and Hygiene, United States (Nov. 2014).

Schneider, I., "Cell Lines Derived from Late Embryonic Stages of *Drosophila melanogaster*," *J. Embryol. Exp. Morph.* 27(2):353-365, Cambridge Univ. Press for the Company of Biologists Ltd, Great Britain (1972).

Schuster, F.L., "Cultivation of *Plasmodium* spp.," *Clinical Microbiology Reviews* 15(3):355-364, American Society for Microbiology, United States (2002).

Seder, R.A., et al., "Protection against Malaria by Intravenous Immunization with a Nonreplicating Sporozoite Vaccine," *Scienceexpress 1-12*, American Association for the Advancement of Science, United States (Aug. 8, 2013); later published as Science 341(6152):1359-1365 (Sep. 20, 2013).

Sheehy, S.H., et al., "Optimising Controlled Human Malaria Infection Studies using Cryopreserved *P. falciparum* Parasites Administered by Needle and Syringe," *PLoS One* 8(6):e65960:1-9, Public Library of Science, United States (2013).

Sirima, S.B., et al., "Protection against malaria by MSP3 candidate vaccine," *N Engl J Med* 365(11):1062-1064, Massachusetts Medical Society, United States (2011).

Terzakis, J.A., et al., "The transformation of the *Plasmodium gallinaceum* oocyst in *Aedes aegypti* mosquitoes," *J Cell Biol* 34(1):311-326, Rockefeller University Press, United States (1967).

Trager, W. and Jensen, J.B., "Human Malaria Parasites in Continuous Culture," *Science* 193(4254):673-675, American Association for the Advancement of Science, United States (1976).

Vanderberg, J.P., "Development of infectivity by the *Plasmodium berghei* sporozoite," *J Parasitol* 61(1):43-50, American Society of Parasitologists, United States (1975).

Vaughan, J.A., et al., "Sporogonic Development of Cultured *Plasmodium falciparum* in Six Species of Laboratory-Reared *Anopheles* Mosquitoes," *Am. J. Trop. Med. Hyg.* 51(2):233-243, The American Society of Tropical Medicine and Hygiene, United States (1994).

(56) References Cited

OTHER PUBLICATIONS

Vaughan, A.M., et al., "Complete *Plasmodium falciparum* liver stage development in liver-chimeric mice," *J Clin Invest 122*(10):3618-3628, American Society for Clinical Investigation, United States (2012).

Vaughan, A.M., et al., "Development of humanized mouse models to study human malaria parasite infection," *Future Microbiol 7*(5):657-665, Future Medicine Ltd, England (2012).

Warburg, A. and Miller, L.H., "Sporogonic Development of a Malaria Parasite in Vitro," *Science 255*(5043):448-450, American Association for the Advancement of Science, United States (1992).

Warburg, A. and Schneider, I., "In Vitro Culture of the Mosquito Stages of *Plasmodium falciparum,*" *Experimental Parasitology 76*(2):121-126, Academic Press, Inc., United States (1993).

Wikipedia, "List of countries by number of military and paramilitary personnel," https://en.wikipedia.org, accessed at http://en.wikipedia.org/wiki/List_of_countries_by_size_of_armed_forces, accessed on Mar. 25, 2016, 11 pages.

World Health Organization, "World Malaria Report 2008," http://apps.who.int, accessed at http://whqlibdoc.who.int/publications/2008/9789241563697_eng.pdf, accessed on Mar. 25, 2016, 215 pages.

World Health Organization, World Malaria Report 2013, available at http://www.who.int/malaria/publications/world_malaria_report_2013/en/, accessed on Mar. 24, 2016, 284 pages.

World Health Organization, "Rainbow Table Reference List," http://www.who.int, accessed at http://www.who.int/vaccine_research/links/Rainbow/en/index.html, accessed on Mar. 24, 2016, 28 pages.

Yeh, S. and Rubin, E.S., "A review of uncertainties in technology experience curves," *Energy Economics 34*:762-771, Elsevier B.V., Netherlands (2012).

Hillyer J.F., et al., "Efficiency of salivary gland invasion by malaria sporozoites is controlled by rapid sporozoite destruction in mosquito hemocoel," Int J Parasitol. 37(6):673-681, Elsevier, Netherlands (2007).

Kennedy M., et al., "A rapid and scalable density gradient purification method for *Plasmodium sporozoites*," Malaria Journal 11:421, Biomed Central Ltd., United Kingdom (2012).

King J.G., et al., "Members of the salivary gland surface protein (SGS) family are major immunogenic components of mosquito saliva," J Biol Chem. 286(47):40824-34, American Society for Biochemistry and Molecular Biology, United States (2011).

Menard, R., "Knockout malaria vaccine?" Nature 433:113-4, Nature Publishing Group, England (2005).

Vaughan, J.A., et al., "Population Dynamics of Plasmodium Falicparum sporogony in laboratory-infected Anopheles Gambiae," J. Parasitol. 78(4): 716-724, Elsevier, Netherlands (1992).

\* cited by examiner

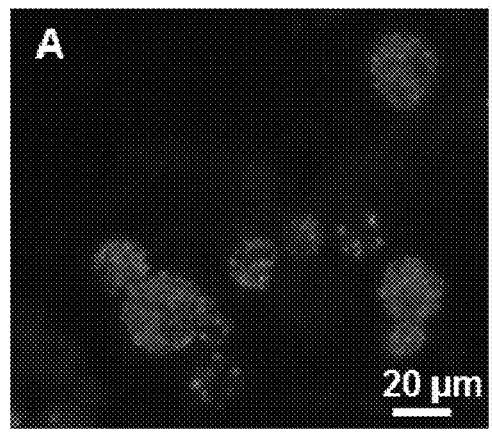 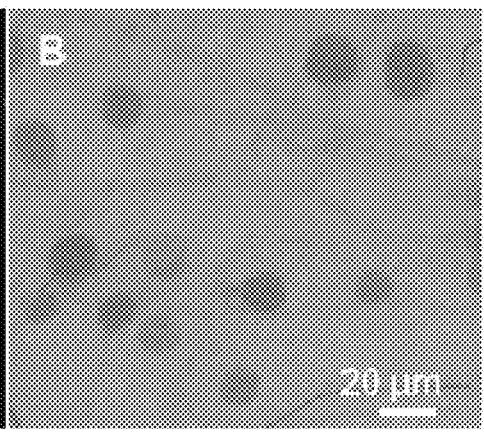
FIG. 5A FIG. 5B
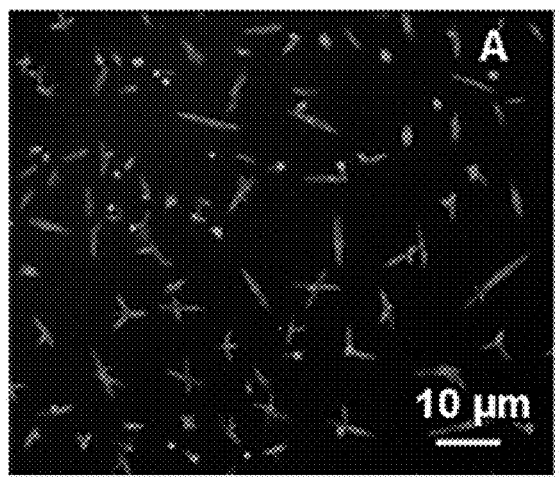 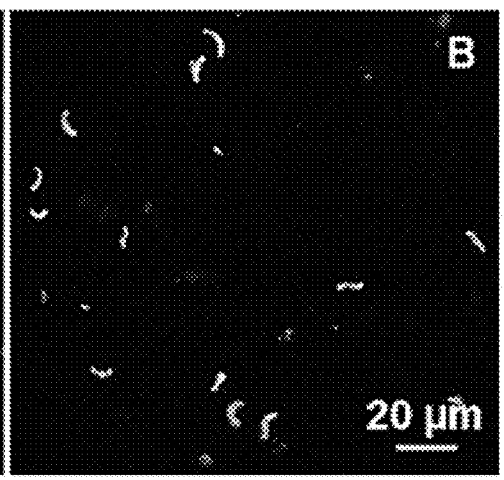
FIG. 6A FIG. 6B

INFECTIOUS PLASMODIUM SPOROZOITES GROWN IN VITRO

CROSS REFERENCE TO RELATED APPLICATIONS

This application is a continuation application of U.S. application Ser. No. 15/095,360, filed Apr. 11, 2016, now U.S. Pat. No. 9,878,026, which is a continuation application of international application PCT/US2015/028890, filed May 1, 2015, which claims priority to U.S. Provisional Appl. No. 61/987,834, filed May 2, 2014, and U.S. Provisional Appl. No. 62/016,981, filed Jun. 25, 2014, the contents of each are hereby incorporated by reference in their entireties.

STATEMENT OF GOVERNMENT SUPPORT

This invention was made with government support under grant number 1R43AI085740-01 awarded by the National Institute of Health (NIH) and under Contract No: W81XWH-16-2-0025 awarded by the Department of Defense/Congressionally Directed Medical Research Programs (CDMRP). The government has certain rights in the invention.

BACKGROUND OF THE INVENTION

Field of the Invention

This invention relates generally to the fields of parasitology, malaria research, and malaria vaccine development. More particularly it relates to *Plasmodium* sporozoites of human host range and the in vitro culturing of the mosquito stages of infectious *Plasmodium* parasites of human host range, particularly to sporozoite stage, and the use of in vitro cultured *Plasmodium* sporozoites as an immunogenic component of vaccines and other reagents.

Background of the Invention

Annually, *Plasmodium falciparum* (Pf) malaria causes >200 million clinical cases, more than 600,000 deaths, and is responsible for loss of greater than $12B of Gross Domestic Product in Africa [1-3]. Malaria is also a serious concern for travelers and military personnel. During 2010-2011 the number of cases of malaria in travelers from the United Kingdom increased by 30% [4]. In 2011, the U.S. had more cases of malaria than in any year in the past 40 years [5, 6]. In all U.S. military campaigns in highly malarious areas during the past 150 years, U.S. forces have had more casualties from malaria than from hostile fire [7]. A highly effective vaccine will have a dramatic impact on the roughly 2.5 billion "at-risk" individuals in the Global Health market.

The world community is now spending approximately $2 billion annually to control malaria through use of insecticide-impregnated bednets, insecticides, and antimalarial drugs. This amounts to approximately $80 per year for every child born in Africa, and in some locations 5 to 10 times that amount is being spent. These approaches are having an excellent effect in many areas. However, drug and insecticide resistance is still developing, and the ability of financial donors and local governments to sustain this effort is limited. It is clear that elimination of malaria from high transmission areas will require new tools. As described in a 2010 editorial, a highly effective vaccine would be the ideal tool for prevention, control and elimination of malaria worldwide:

"What is still needed is the only tool that has ever truly conquered any infectious disease: an effective . . . affordable vaccine . . . here, the global malaria community has been too complacent . . . GlaxoSmith-Kline's . . . RTS,S plus adjuvant AS01 is a first-generation pre-erythrocyte-stage vaccine with modest and time-limited efficacy . . . We cannot afford to wait a further 20 years for the next generation . . . vaccines . . . ."

Anonymous, The Lancet, Apr. 24, 2010

And as described in a 2011 malERA initiative report, the ideal vaccine would be a pre-erythrocytic-stage vaccine that prevents parasites from getting out of the liver into the bloodstream, thereby preventing disease as well as transmission [8]. This has been termed a "vaccine that interrupts malaria transmission" ('VIMT').

Glaxo Smith Kline has developed a vaccine candidate termed RTS,S/AS01, which uses a recombinant protein (that fuses part of the Pf circumsporozoite protein (CSP) with hepatitis B surface antigen) with a strong adjuvant (AS01). Recent Phase 3 trials [9-12] in 5-27 month old humans demonstrated a 36% reduction in the incidence of malaria during a year and a 56% reduction in the rate at which malaria was acquired during the first year, and a 47% reduction in severe malaria during the first year. Unfortunately, the results in infants were not as strong. In 6-12 week old humans, the vaccine demonstrated a 16% reduction in the incidence of malaria during a year, a 31% reduction in the rate at which malaria was acquired during the first year, and a 36% reduction in severe malaria (26% by intention to treat) during the first year. These results have been called disappointing and would not qualify this vaccine as highly effective or as a VIMT.

During the last ten years, the focus for the development of a highly effective VIMT malaria vaccine has shifted in part to the utilization of the whole parasite, sporozoite (SPZ) stage, of *Plasmodium* as the vaccine immunogen. In a recently completed study at the Vaccine Research Center (VRC) at National Institute of Allergy and Infectious Disease (NIAID), the Sanaria® PfSPZ Vaccine, composed of radiation attenuated Pf SPZ, was administered by intravenous (IV) injection and protected 6 of 6 (100%) of the volunteers who received the highest dose. There was a dose response in regard to protective efficacy (6/9 protected at next lower total dose) and a significant correlation between titers of antibodies against Pf SPZ and protection. Sanaria® PfSPZ Vaccine is therefore demonstrably potent and highly protective in humans. These historic results were published online in *Science* in August 2013 and in print in September 2013 [13].

SPZ are also being used as the parasite component of an infection and treatment approach to vaccination called Sanaria® PfSPZ-CVac, in which live infectious *Plasmodium* SPZ are administered in the presence of an asexual erythrocytic stage anti-malarial such as chloroquine [14].

Finally, live infectious Pf SPZ are being used for controlled human malaria infections (CHMI) as a means for testing malaria vaccines and other therapeutics [15, 16].

Substantially purified *Plasmodium* sporozoites prepared from salivary glands extracted from mosquitoes and grown in culture are described in U.S. Pat. No. 8,043,625, which is incorporated herein by reference.

Presently, the whole parasite Pf SPZ used in the vaccines and reagents described above have been obtained by rearing aseptic *Anopheles* mosquitoes, infecting them with aseptic Pf gametocytes, permitting the Pf parasites to progress through sporogony in vivo within the mosquito, to the sporozoite stage, and then hand dissecting the salivary glands from the mosquitoes and isolating and purifying the aseptic sporozoites (U.S. Pat. Nos. 7,229,627; 8,367,810) [17]. While this manufacturing approach is capable of producing sufficient quantities of live, aseptic purified Pf SPZ for use in all the clinical trials for these products, the methodology is labor intensive and requires substantial resources for insect husbandry and parasite dissection. In particular, dissecting from the mosquito salivary glands is a technical and time-consuming step in the production of Pf SPZ and other *Plasmodium*-species SPZ of human host range.

The mosquito host stages of *Plasmodium* parasite development are shown in FIG. 1. While efforts to establish the asexual portion (vertebrate-host stages) of the *Plasmodium* life cycle in vitro have been successful [18] substantial effort has been made to accomplish the same for the sexual (mosquito-host stages) and sporogonic portion, but these efforts have been unsuccessful for producing clinically relevant infectious *Plasmodium* sporozoites of human host range, particularly Pf SPZ. In vitro transformation of *P. gallinaceum* (avian host range) and Pf ookinetes resulted in low numbers of oocysts and SPZ, but infectivity of these sporozoites was never demonstrated [19-20]. In vitro transformation of *P. berghei* (rodent host range) produced oocysts and SPZ, but the SPZ were much less infective than were mosquito-derived SPZ [21].

SUMMARY OF THE INVENTION

Provided herein are in vitro-reared infectious *Plasmodium* sporozoites (SPZ) of human host range, particularly *Plasmodium falciparum* (Pf) SPZ, wherein sporogony from gametocyte stage to sporozoite stage is external to mosquitoes. In some embodiments, the in vitro-reared infectious *Plasmodium* sporozoites are absent any attendant mosquito material.

Additionally provided are cultures of in vitro-reared *Plasmodium* parasites of human host range, particularly Pf parasites, wherein said parasites have undergone sporogonic development in vitro. In some embodiments, cultures are absent any attendant mosquito material.

Additionally provided are methods of culturing *Plasmodium* sporozoites of human host range in vitro during sporogonic development of said sporozoites, said method comprising culturing human host range *Plasmodium* gametocytes in the presence of red blood cells in an exflagellation culture medium, agglutinating the red blood cells using a lectin, collecting a mixture (e.g. a pellet) comprising zygotes, gametes, gametocytes and agglutinated cells, culturing the collected mixture (e.g., the pellet) on a substrate comprising a matrix and in an ookinete culture medium, exchanging medium and continuing the culture in an oocyst medium and harvesting the *Plasmodium* sporozoites produced thereby.

Also provided are methods for increasing production of human host range *Plasmodium* oocysts relative to oocyst production from an equivalent number of human host range *Plasmodium* gametocytes in a mosquito, comprising culturing human host range *Plasmodium* gametocytes in an exflagellation culture medium, collecting a mixture (e.g. a pellet) comprising zygotes, gametes, gametocytes and agglutinated cells, culturing the collected mixture (e.g., the pellet) on a substrate comprising a matrix and in an ookinete culture medium, changing medium and continuing the culture in an oocyst medium and quantifying the number of *Plasmodium* oocysts, wherein said method produces more oocysts developed in vitro compared to oocysts of the same species developed in mosquitoes from an equivalent number of *Plasmodium* gametocytes.

Also provided are methods of inducing an immune response in a subject against *Plasmodium*-species specific antigens, comprising administering *Plasmodium*-reared sporozoites of human host range to the subject.

Also provided are vaccine compositions comprising in vitro-reared *Plasmodium* sporozoites of human host range. In some embodiments, the vaccine is absent any attendant mosquito material.

The inventions disclosed herein provide, e.g., the following innovations: i) achieving an average 39-fold more oocysts developed in vitro compared to oocysts of the same *Plasmodium* species developed in mosquitoes and from an equivalent number of stage V gametocytes; ii) producing in vitro-reared, infective Pf SPZ; and iii) reaching infectivity of human liver cells by in vitro-produced Pf SPZ that is at least as efficient as mosquito-produced Pf SPZ.

This work stands out as being unique in the quantity of Pf SPZ produced from a given number of gametocytes in vitro, and in the demonstration of fully functional infectious activity of the in vitro-produced Pf SPZ. For example, it is described herein that in vitro-produced Pf SPZ successfully invaded the human hepatocyte cell line HC-04 [24,25], and developed to schizonts expressing merozoite surface protein 1 (Pf MSP1), a protein demonstrating infectivity; and it was demonstrated that this in vitro infectivity was at least as efficient as that of mosquito-produced Pf SPZ.

DESCRIPTION OF THE DRAWINGS

FIG. 2A shows early retort, midstage retort, and late stage retort (from left to right) and FIG. 2B shows mature ookinetes. Parasites were taken from a gametocyte culture 18 days post induction. Early retorts are first seen about 14 hours and ookinetes from 24 hours after initiation of the ookinete culture. Giemsa-stained smears of cultures were shown.

FIGS. 5A-5B show 7 day oocysts in vitro (FIG. 5A) and in mercurochrome stained mosquito midgut (FIG. 5B).

FIGS. 6A-6B show in vitro-produced Pf SPZ: (FIG. 6A) Pf SPZ developed in culture well detected after fixation of the well and (FIG. 6B) extracted Pf SPZ. Both detected by IFA using fluorescently labelled anti-Pf CSP mAb.

FIG. 8A & FIG. 8B show phase contrast images of oocysts in cellometer used for quantification and FIG. 8C shows IFA of extracted oocysts in suspension (not permeabilized) using fluorescently labeled anti-Pf CSP mAb.

DETAILED DESCRIPTION OF THE INVENTION

Definitions

Figure 1:
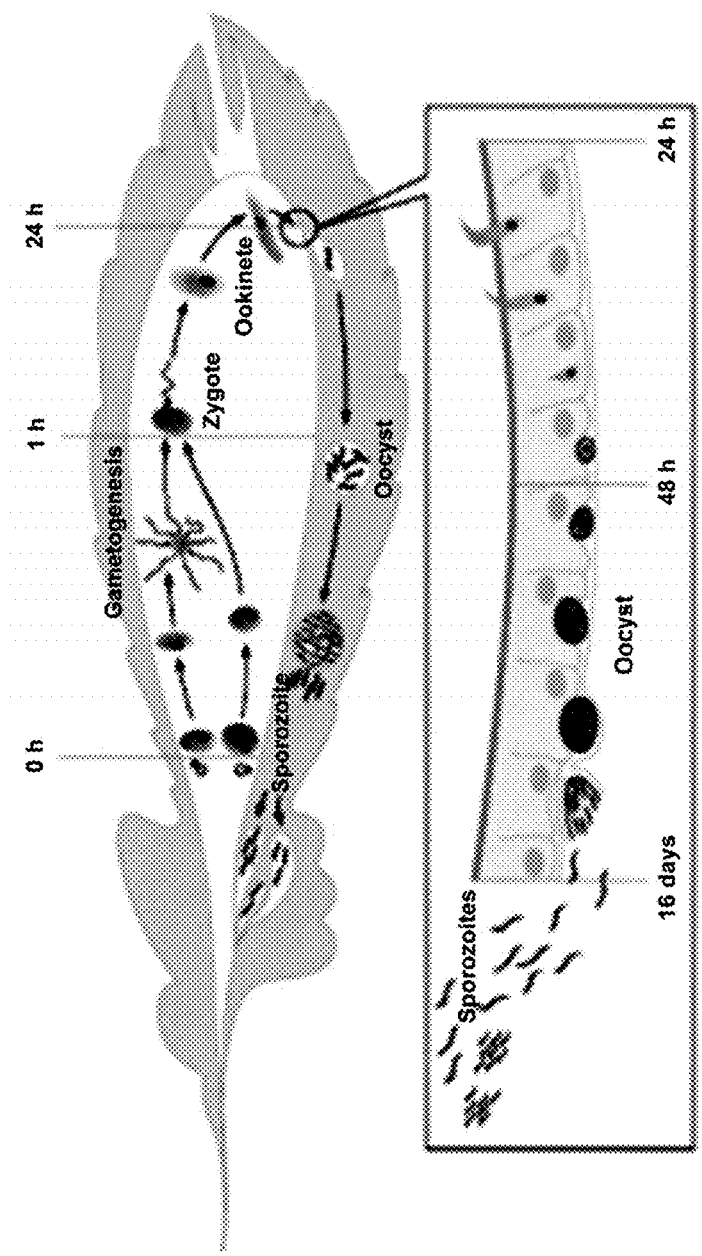
FIG. 1 illustrates the sporogonic development of *Plasmodium falciparum* in the mosquito.

As used herein with regard to parasite development "in vitro" means independent of and external to an intact host organism (also referred to as a whole host organism). For example, in vitro development of a *Plasmodium* parasite of human host range includes culturing parasites that advance through developmental stages external to and independent of a live animal host, e.g., mosquitoes.

As used herein, "rearing" or "reared" means promoting and supporting the orderly and ontogenic progression of *Plasmodium* growth and development.

As used herein, "sporogony" (or sporogonic development) means the orderly and ontogenic progression of *Plasmodium* development through characteristic sexual stages from gametocyte to sporozoite.

As used herein "*Plasmodium* species of human host range" (used interchangeably with human host range *Plasmodium* species, *Plasmodium* parasites of human host range, and human host range *Plasmodium* parasites) include *Plasmodium* of the following species: *P. falciparum, P. vivax, P. ovale, P. malariae*, and *P. knowlesi*.

As used herein, "culture", in the context of in vitro-reared *Plasmodium* parasites of human host range, means a system external to a live animal host (e.g. mosquitoes) comprising a medium and *Plasmodium* parasites of human host range. In certain embodiments, the culture further comprises a substrate.

"Substrate" as used herein means a growth surface. In some embodiments, the substrate comprises a cell culture matrix, e.g., comprising a polystyrene matrix and/or Matrigel [27, 28].

"Medium" as used herein means a nutrient composition. In certain embodiments, the medium is an exflagellation medium, which facilitates the emergence of gametes from gametocytes, which then undergo fertilization to zygotes, e.g., by mimicking mosquito lumen conditions after a blood meal. In certain embodiments, the medium is an ookinete medium, which facilitates the differentiation of zygotes to ookinetes. In certain embodiments, the medium is an oocyst medium, which provides nutrients for the in vitro sporogony to sporozoite stage.

"Suitable for human pharmaceutical use" as used herein refers to having a sufficient quantity, sterility (asepticity), and purity for approved clinical use in humans, for example, acceptable according to FDA or USP standards.

"Aseptic" as used herein means absent the introduction or presence of detectable microorganism contamination such as bacteria, fungi, pathologic viruses and the like. An aseptic method of sporozoite preparation results in a sterile preparation of sporozoites—free of any other type of microorganism or infectious agent. Aseptic preparation of a sterile composition is required for clinical and pharmaceutical use. Microbiological assays used to monitor an aseptic methodology assess the presence or absence of contamination. They include, but are not limited to, the Microbial Limits Test, current USP <61>, and sterility test, current USP <71>, incorporated herein by reference.

"Attendant material" as used herein refers to material in a culture or preparation of sporozoites, which is not the medium or a component of the medium, or a carrier or excipient, and is not specific to the sporozoites per se. In certain embodiments attendant material includes, e.g., biological debris. In some embodiments attendant material is a consequence of the means by which sporozoites are produced.

"Attendant mosquito material" as used herein is biological material or debris derived from and specific to a mosquito.

"Conferring protective immunity" as used herein refers to providing to a population or a host (i.e., an individual) the ability to generate an immune response protective against a disease (e.g., malaria) caused by a pathogen (e.g., *Plasmodium falciparum*) such that upon challenge, the clinical manifestations, pathology, or symptoms of disease in a host are reduced as compared to a non-treated host, or such that the rate at which infection, or clinical manifestations, pathology, or symptoms of disease appear within a population are reduced, as compared to a non-treated population.

"Immune response" as used herein in the context of a *Plasmodium*-specific antigen means a response in the recipient to the introduction of sporozoites, generally characterized by, but not limited to, production of antibodies and/or cellular immune responses. Generally, an immune response may be a cellular response such as induction or activation of CD4+ T cells or CD8+ T cells specific for *Plasmodium*-species epitopes, a humoral response of increased production of *Plasmodium*-specific antibodies, or both cellular and humoral responses. With regard to a malaria vaccine, the immune response established by a vaccine comprising sporozoites includes but is not limited to responses to proteins expressed by extracellular sporozoites or other stages of the parasite after the parasites have entered host cells, especially hepatocytes and mononuclear cells such as dendritic cells and/or to components of said parasites. In an embodiment of the instant invention, the immune response is a measurable antibody and/or cellular response to sporozoite-specific antigens. In other embodiments, upon subsequent challenge by infectious organisms the immune response prevents development of pathogenic parasites to the erythrocytic stage that causes disease.

"Vaccine" as used herein is a preparation comprising an immunogenic agent and a pharmaceutically acceptable diluent potentially in combination with excipient, adjuvant and/or additive or protectant. The immunogen may be comprised of a whole infectious agent or a molecular subset of the infectious agent (produced by the infectious agent, synthetically or recombinantly). When the vaccine is administered to a subject, the immunogen stimulates an immune response that will, upon subsequent challenge with infectious agent, protect the subject from illness or mitigate the pathology, symptoms or clinical manifestations caused by that agent. A therapeutic (treatment) vaccine is given after infection and is intended to reduce or arrest disease progression. A preventive (prophylactic) vaccine is intended to prevent initial infection or reduce the rate or burden of the infection. Agents used in vaccines against a parasitic disease such as malaria can be whole-killed (inactive) parasites, live parasites, live-attenuated parasites (unable to fully progress through their life cycle), or purified or artificially manufactured molecules associated with the parasite—e.g. recombinant proteins, synthetic peptides, DNA plasmids, and recombinant viruses or bacteria expressing *Plasmodium* proteins. A vaccine may comprise sporozoites along with other components such as excipient, diluent, carrier, preservative, adjuvant or other immune enhancer, or combinations thereof, as would be readily understood by those in the art.

"Attenuation" as used herein means a gene alteration or mutation of an organism such as a *Plasmodium* parasite, such that it loses its ability to complete its normal life cycle, but rather it arrests at a particular stage of development. In the *Plasmodium* organisms of the instant invention, the functions of one or more genes of a radiation attenuated or genetically attenuated parasite (GAP) are disrupted such that the attenuated mutant retains the ability to infect a host and invade hepatocytes within the liver, but arrests development in liver-stage.

"Hepatocyte Invasion" as used herein refers to the ability of the sporozoite-stage of the *Plasmodium* parasite to seek out and enter particular target cells, in this case, host hepatocytes, either hepatocyte cells in culture [24,25] or, hepatic cells in vivo after initial introduction into the circulatory system of a host. Non-attenuated parasites would then undergo further stage-specific development.

"Metabolically active" as used herein means alive and capable of performing sustentative functions and some life-cycle processes. With regard to attenuated sporozoites this includes but is not limited to sporozoites capable of invading hepatocytes in culture and in vivo, potentially having a limited capacity to divide and progress through some developmental stages within the liver, and de novo expression of stage-specific proteins.

In Vitro Sporozoites

Disclosed are compositions of in vitro-reared live, infectious sporozoites, particularly *Plasmodium* sporozoites—attenuated sporozoites as well as pathogenic sporozoites. In certain embodiments, the application is directed to cultures of in vitro-reared *Plasmodium* sporozoites of human host range wherein sporogony from gametocyte stage to sporozoite stage is external to mosquitoes. In some embodiments, the in vitro-reared infectious *Plasmodium* sporozoites are absent any attendant mosquito material. In certain embodiments, sporogony from gametocyte stage to sporozoite stage has occurred external to mosquitoes.

In some embodiments, the in vitro-reared *Plasmodium* sporozoites are at least 70%, 80%, or 90% as infectious to human hepatocytes as *Plasmodium* sporozoites of human host range reared in a mosquito. In some embodiments, the in vitro-reared *Plasmodium* sporozoites are between 70-100%, 80-100%, or 90-100% as infectious to human hepatocytes as *Plasmodium* sporozoites of human host range reared in a mosquito. In some embodiments, the infectivity is measured in vitro or in vivo.

In some embodiments, the infectivity is measured using an in vitro Pf 6-Day Hepatocyte Potency Assay used to determine the ability of in vitro Pf SPZ to infect HC-04 (1F9) cells (a human hepatic cell line) [24,25] and develop into late liver stage parasites expressing PfMSP-1 [15]. An example of such a method can include:

a. Cell culture and seeding of ECL-coated Lab-Tek slides. Coat 8 well Permanox Lab-Tek chamber slides with ECL Cell Attachment Matrix for 1-2 hours at 37±2° C. Dilute HC-04 (1F9) cells with complete DMEM/F-12 medium (CM) to seed at $4\times10^4$ viable cells in 0.3 mL per well. Wash and incubate for 24±4 h at 37±2b° C. and 5±2% $CO_2$;

b. Infection and Calculation of the number of SPZ added per well: Centrifuge the in vitro-produced Pf sporozoites for 2 minutes at 13,200 rpm (relative centrifugal force 16,100) at 22±2° C. using a fixed angle rotor. Discard the supernatants and resuspend the pellets in CM. Aspirate and discard medium from each well of the Lab Tek slide. Add 50 µL of in vitro SPZ suspension/well in triplicate. Dilute the infecting sporozoite suspension 1:10 in CM and count the number of sporozoites using a Cellometer and a phase contrast microscope, and calculate the number of SPZ added per well. Incubate the chamber slides at 37±2° C. and 5±2% $CO_2$ for 3 h±10 min. Wash monolayer 3 times with 0.3 mL DMEM/F-12 complete medium by gently aspirating excess culture medium containing sporozoites from each well using 1000 µL pipet tips, being careful not to contaminate control wells with Pf SPZ. After final wash, add 0.3 mL of DMEM/F-12 complete medium to each well;

c. Maintenance of Cultures: The culture medium is changed daily to ensure successful development of liver stages and maintenance of cultures. Chamber slides cultures are fixed with ice-cold methanol 6 days post infection. Store at 4±2° C.;

d. Staining for Indirect Immuno-fluorescencent Assay (IFA): Discard PBS from the slides then add 2-3 drops of image iT-FX signal enhancer to each well and incubate at 37±2° C. for 30±3 minutes. Discard image enhancer solutions and wash cultures 3 times with PBS. Add 100 µL of diluted anti-PfMSP-1 monoclonal mouse antibody to triplicate wells and incubate at 37±2° C. for 60-70 minutes. At the end of the incubation period, discard antibody solutions and wash with PBS. Dilute Alexa Fluor 488 anti-mouse IgG at 1:200 in PBS with 0.02% Evan's blue. Add 100 µL of diluted Alexa 488 anti-mouse IgG to triplicate wells Incubate the slides at 37±2° C. for 60-70 minutes. Mount coverslip using Vectashield mounting medium with DAPI and store at 2-8° C., away from light, until time of observation; and e. Evaluation and enumeration of Pf liver stages: Using an epifluorescence microscope at 400× magnification, evaluate and record number of Pf liver stages/well that show antibody reactivity. Count the number of liver stage parasites in all three wells and report the average.

In some embodiments, the in vitro-reared *Plasmodium* sporozoites are aseptic. In some embodiments, the in vitro-reared *Plasmodium* sporozoites have reduced risk of contamination with attendant material from a host organism, e.g., a mosquito (as might be the case with sporozoites dissected from the salivary glands of host mosquitoes).

In some embodiments, the in vitro-reared *Plasmodium* sporozoites are of human host range. In some embodiments, the species of in vitro-reared *Plasmodium* sporozoites is *P. falciparum*.

In some embodiments, the in vitro-reared *Plasmodium* sporozoites are suitable for pharmaceutical use. In some embodiments, the in vitro-reared *Plasmodium* sporozoites are used in a vaccine. In some embodiments the in vitro-reared *Plasmodium* sporozoites are attenuated.

In vitro-reared Pf SPZ are tested for their ability to invade and develop in human hepatocytes in culture. In vitro-reared PfSPZ can also be tested in vivo for the ability to complete the Pf life cycle. This can be done by using human liver chimeric mice transfused with human blood.

Cultures

In certain embodiments, the application is directed to a culture of in vitro-reared *Plasmodium* parasites of human host range wherein said parasites are undergoing or have undergone sporogonic development in vitro.

In certain embodiments, the culture comprises *Plasmodium* parasites of human host range at an equivalent stage of sporogonic development. In certain embodiments, the culture is able to maintain continued sporogonic development of *Plasmodium* parasites of human host range.

In some embodiments, the parasites have reached sporozoite stage of development. In some embodiments, the in vitro-reared *Plasmodium* sporozoites of human host range are at least 70%, 80%, or 90% as infectious of hepatocytes as *Plasmodium* sporozoites of the same species reared in a mosquito. In some embodiments, the in vitro-reared *Plasmodium* sporozoites of human host range are between 70-100%, 80-100%, or 90-100% as infectious of human hepatocytes as *Plasmodium* sporozoites of the same species reared in a mosquito. In some embodiments, infectivity is measured in cultures of HC-04 cells, in some embodiment infectivity is measured by hepatic infection in vivo.

Some embodiments are directed to a culture of in vitro-reared infectious *Plasmodium* sporozoites of human host range wherein said culture is absent any attendant mosquito material and wherein said in vitro-reared *Plasmodium* sporozoites are at least 70%, 80%, or 90% as infectious of human hepatocytes as *Plasmodium* sporozoites of human host range, and of the same species, reared in a mosquito. In some embodiments, the in vitro-reared *Plasmodium* sporozoites are between 70-100%, 80-100%, or 90-100% as infectious of human hepatocytes as *Plasmodium* sporozoites of human host range, and of the same species, reared in a mosquito.

In some embodiments, the culture comprises a first (referred to as exflagellation) medium, which facilitates the emergence of gametes from gametocytes, e.g., by mimicking mosquito lumen conditions after a blood meal. In some embodiments, the exflagellation medium comprises fetal bovine serum (FBS), glucose, sodium bicarbonate and xanthurenic acid. In some embodiments, the exflagellation medium comprises 10-30%, 15-25%, or 18-22% FBS. In some embodiments, the exflagellation medium comprises 0.05% to 0.5%, 0.075% to 0.5%, or 0.075% to 0.25% glucose. In some embodiments, the exflagellation medium comprises 0.05% to 0.5%, 0.075% to 0.5%, or 0.075% to 0.25% sodium bicarbonate. In some embodiments, the exflagellation medium comprises 0.01% to 0.05%, 0.01% to 0.04%, or 0.02% to 0.04% xanthurenic acid. In some embodiments, the exflagellation medium comprises FBS, 0.05% to 0.5% glucose (e.g., 0.1%), 0.05% to 0.5% sodium bicarbonate (e.g., 0.1%) and 0.01% to 0.05% xanthurenic acid (e.g., 0.022%).

In some embodiments, the first medium is removed and the culture comprises a second (referred to as ookinete) medium, which facilitates the differentiation of zygotes to ookinetes and the invasion of ookinetes into a 3D matrix substrate. In some embodiments, the ookinete medium comprises FBS, RPMI, and trehalose. In some embodiments, the ookinete medium comprises 10-30%, 15-25%, or 18-22% FBS. In some embodiments, the ookinete medium comprises 0.1% to 0.5%, 0.15% to 0.3%, or 0.2% to 0.3% trehalose. In some embodiments, the ookinete medium comprises 0.1% to 0.5%, 0.15% to 0.3%, or 0.2% to 0.3% dextrose. In some embodiments, the ookinete medium comprises 0.01% to 0.08%, 0.02% to 0.06%, 0.03% to 0.05% sodium bicarbonate. In some embodiments, the ookinete medium further comprises an antibiotic. In some embodiments, the antibiotic is penicillin, streptomycin, or a combination thereof. In some embodiments, the ookinete medium comprises an antibiotic at 1 to 50 units/mL, 1 to 40 units/mL, 5 to 30 units/mL, or 10 to 20 units/mL. In some embodiments, the ookinete medium comprises an antibiotic at 1 to 50 μg/mL, 1 to 40 μg/mL, 5 to 30 μg/mL, or 10 to 20 μg/mL. In some embodiments, ookinete medium comprises of RPMI medium containing 10-30% FBS (e.g., 20%), 0.1% to 0.5% trehalose (e.g., 0.25%), 0.1% to 0.5% dextrose (e.g., 0.25%), 0.01% to 0.08% sodium bicarbonate (e.g., 0.04%), 1 to 50 units/mL penicillin (e.g., 10 units/mL) and 1 to 50 μg/mL streptomycin (e.g., 10 μg/mL).

In some embodiments, the second medium is removed and the culture comprises a third (referred to as oocyst) medium, which provides nutrients for the in vitro sporogony of the *Plasmodium* parasites to sporozoite stage. In some embodiments, the oocyst medium comprises Schneider's *Drosophila* medium [26], FBS, sodium bicarbonate, trehalose, hypoxanthine, HEPES, essential amino acids, para-aminobenzoic acid (PABA), antibiotic (e.g., penicillin and streptomycin), lipoproteins, cholesterol, and vitamins. In some embodiments, the oocyst medium comprises 10-30%, 15-25%, or 18-22% FBS. In some embodiments, the oocyst medium comprises 0.01% to 0.08%, 0.02% to 0.06%, 0.03% to 0.05% sodium bicarbonate. In some embodiments, the oocyst medium comprises 0.1% to 0.5%, 0.15% to 0.3%, or 0.2% to 0.3% trehalose. In some embodiments, the oocyst medium comprises 10 to 100 μg/mL, 20 to 100 μg/mL, 25 to 75 μg/mL, or 40 to 60 μg/mL hypoxanthine. In some embodiments, the oocyst medium comprises 0.05M to 0.25M, 0.075M to 0.2M, or 0.075M to 1.5M HEPES. In some embodiments, the oocyst medium comprises 0.01% to 0.08%, 0.02% to 0.06%, 0.03% to 0.05% PABA. In some embodiments, the oocyst medium further comprises an antibiotic. In some embodiments, the antibiotic is penicillin, streptomycin, or a combination thereof. In some embodiments, the oocyst medium comprises an antibiotic at 1 to 50 units/mL, 1 to 40 units/mL, 5 to 30 units/mL, or 10 to 20 units/mL. In some embodiments, the oocyst medium comprises an antibiotic at 1 to 50 μg/mL, 1 to 40 μg/mL, 5 to 30 μg/mL, or 10 to 20 μg/mL. In some embodiments, the oocyst medium comprises 0.05% to 0.5%, 0.075% to 0.5%, or 0.075% to 0.25% lipoproteins. In some embodiments, the oocyst medium comprises 0.05% to 0.5%, 0.075% to 0.5%, or 0.075% to 0.25% cholesterol. In some embodiments, the oocyst medium comprises Schneider's *Drosophila* medium, 10-30% FBS (e.g., 20%), 0.01% to 0.08% sodium bicarbonate (e.g., 0.04%), 0.1% to 0.5% trehalose (e.g., 0.25%), 10 to 100 μg/mL hypoxanthine (e.g., 50 μg/mL), 0.05M to 0.25M HEPES (e.g., 0.1M), essential amino acids (e.g., 1×, GIBCO), 0.01% to 0.08% para-aminobenzoic acid (PABA, e.g., 0.04 μg/mL), 1 to 50 units/mL penicillin (e.g., 10 units/mL) and 1 to 50 μg/mL streptomycin (e.g., 10 μg/mL), 0.05% to 0.5% lipoproteins (e.g., 1.5%), 0.05% to 0.5% cholesterol (e.g., 0.1%), and vitamins (e.g., 1×, GIBCO).

In some embodiments, the culture substrate comprises a 3D culture matrix. In some embodiments, the 3D culture matrix is pre-seeded with *Drosophila* Schneider S2 cells [26]. In some embodiments, the culture matrix comprises polystyrene matrix (e.g., AMS Biotechnology Ltd, UK) coated with Matrigel [27, 28]. For example, polystyrene matrix can be coated with Matrigel by carefully layering 1 mg/mL of Matrigel on top of the polystyrene matrix followed by incubation at 37° C. In some embodiments, the culture matrix comprises polystyrene matrix, Matrigel, and *Drosophila* Schneider S2 cells. In some embodiments, the matrix is coated with an extracellular matrix protein, e.g., a laminin, a collagen, or a combination thereof.

In some embodiments, the culture is aseptic. In some embodiments, the sporozoites derived from the culture are suitable for pharmaceutical use.

Methods of Culturing *Plasmodium* Parasites Disclosed are methods of culturing *Plasmodium* parasites and/or making cultures of in vitro-reared live, infectious *Plasmodium* sporozoites and methods of culturing and/or making compositions of in vitro-reared attenuated *Plasmodium* sporozoites.

In certain embodiments, the application is directed to methods of culturing *Plasmodium* parasites of human host range in vitro during sporogonic development of said parasites, comprising:

a. Culturing human host range *Plasmodium* gametocytes in the presence of red blood cells in an exflagellation culture medium,
b. Agglutinating the red blood cells using a lectin,
c. Collecting a mixture comprising zygotes, gametes, gametocytes and agglutinated cells (in some embodiments this is accomplished by centrifugation and collection of the pellet),
d. Culturing said mixture on a substrate comprising a matrix and in an ookinete medium, wherein said parasites differentiate to ookinetes and said ookinetes enter said matrix and differentiate to oocyst stage,
e. Replacing said ookinete medium with an oocyst culture medium, and
f. Harvesting the *Plasmodium* sporozoite-stage parasites produced thereby.

For example, methods for culturing can include: (a) suspending Stage V gametocytes in exflagellation medium (1 h) (In this step male and female gametes emerge from micro and macro gametocytes and interact (fertilization) to form zygotes); (b) agglutinating erythrocytes by adding lectin, e. g. wheat germ agglutinin, a lectin purified from wheat (1 h); (c) centrifuging the culture suspension to collect the pellet, which contains zygotes, erythrocyte debris and any gametocytes and gametes that had not undergone differentiation; (d) suspending the pellets in ookinete medium and seeding onto a 3D cell culture matrix pre-seeded with *Drosophila* Schneider S2 cells [26]. The 3D culture matrix was developed using Matrigel [27, 28] in 8-well culture plates or in other tissue culture vials or trans well culture inserts. Developed ookinetes then invade into the matrix in the next 20-24 h because they are motile (unlike gametocytes, gametes and zygotes which are not motile); (e) 20-24 h later, trans well inserts or 8-well culture plates are washed to remove any ookinetes that have not invaded into the matrix, as well as remaining gametocytes, gametes and zygotes (which did not develop to ookinetes) and the culture medium is replaced with oocyst medium. Ookinete that are in the matrix transform into oocyst in 12-24 h after invasion. (f) Oocyst medium is changed once in every 2-3 days; (g) 7, 8 and 11 day oocysts are determined on day 7, 8 and 11 day post-initiation of culture; (h) SPZs are harvested from the medium on day 15, 18, and 21 post culture initiations by collecting medium from the 8-well or trans well culture plates, followed by trituration. PfSPZ are counted using a cellometer; Harvested SPZs may then be seeded on HC-04 cells for determining potency using the 6-day hepatocyte potency assay.

In certain embodiments, the human host range *Plasmodium* gametocytes are derived from a culture of human host range *Plasmodium* in red blood cells (erythrocytes), e.g., as disclosed in Trager W, and Jensen J B. Science 193: 673-675, 1976, which is incorporated herein by reference.

Methods of Increased Production of *Plasmodium* Oocysts

In certain embodiments, the application is directed to an in vitro method for increasing the production of *Plasmodium* oocysts compared to oocysts of the same species and developed in mosquitoes from an equivalent number of human host range *Plasmodium* gametocytes comprising:

a. Culturing human host range *Plasmodium* gametocytes in the presence of red blood cells in an exflagellation culture medium,
b. Agglutinating said red blood cells using a lectin,
c. Collecting a mixture comprising zygotes, gametes, gametocytes and agglutinated cells (in some embodiments this is accomplished by centrifugation and collection of the pellet),
d. Culturing said mixture on a substrate comprising a matrix and in an ookinete medium, wherein said parasites differentiate to ookinetes and said ookinetes enter said matrix and differentiate to oocyst stage,
e. Replacing said ookinete medium with an oocyst culture medium,
f. Continuing the parasite culture by replacing the oocyst medium with a oocyst medium containing S2 cells (S2 cells are added to replenish the loss of cells during media change) every 40-80, (preferably, 48-72 hours), and
g. Quantitating the oocyst stage *Plasmodium* parasites of human host range;
h. Wherein said method produces more *Plasmodium* oocysts of human host range developed in vitro compared to oocysts of the same species developed in mosquitoes from the equivalent number of human host range *Plasmodium* gametocytes.

In certain embodiments, the human host range *Plasmodium* gametocytes are derived from a culture of human host range *Plasmodium* in red blood cells (erythrocytes), e.g., as disclosed in Trager (1976).

In some embodiments, the efficiency of transformation of stage V gametocytes to ookinetes in vitro is within the range of 1-25%, 5-25%, 5-21%, or 8-21%.

In some embodiments, the efficiency of transformation of stage V gametocyte to 7, 8, or 11 day oocysts is within the range of 1-15%, 2-14%, 2-25% or 2.4-12.5%.

In some embodiments, at least 10 to 20, 10 to 30, 10 to 39, or 10 to 60-fold more oocysts develop in vitro compared to oocysts developed in mosquitoes from an equivalent number of stage V gametocytes. In some embodiments, 10 to 20, 10 to 30, 10 to 39, or 10 to 60-fold more oocysts develop in vitro compared to oocysts developed in mosquitoes from an equivalent number of stage V gametocytes.

Methods of Use

Disclosed are methods of using in vitro-reared *Plasmodium* sporozoites, and attenuated in vitro-reared *Plasmodium* sporozoites (See for example: U.S. Pat. No. 7,229,627; U.S. Ser. No. 61/783,326, both of which are incorporated herein by reference), as the immunogen in vaccines to prevent malaria. Also disclosed are methods of using in vitro-reared pathogenic parasites useful for assessing the effectiveness of antimalarial drugs and vaccines, and in conjunction with antimalarial agents, particularly antimalarials such as chloroquine, which target the asexual erythrocytic stage of *Plasmodium* infection, useful in vaccine regimens for conferring protective immunity.

In certain embodiments, the in vitro-reared *Plasmodium* sporozoites of human host range of the application are used in a vaccine composition. In some embodiments, the in vitro-reared *Plasmodium* sporozoites of human host range are attenuated. In some embodiments, the in vitro-reared *Plasmodium* sporozoites of human host range are non-attenuated. In some embodiments, the in vitro-reared *Plasmodium* sporozoites of human host range are non-attenuated and used with an anti-malarial agent, e.g., chloroquine. In some embodiments, the in vitro-reared *Plasmodium* sporozoites of human host range induce an immune response in a human subject. In some embodiments, the in vitro-reared *Plasmodium* sporozoites of human host range generate an immune response to the corresponding *Plasmodium* sporozoites, and in some embodiments, the in vitro-reared *Plasmodium* sporozoites of human host range provide protective immunity to a human subject.

EXAMPLES

Example 1

Figure 2A:
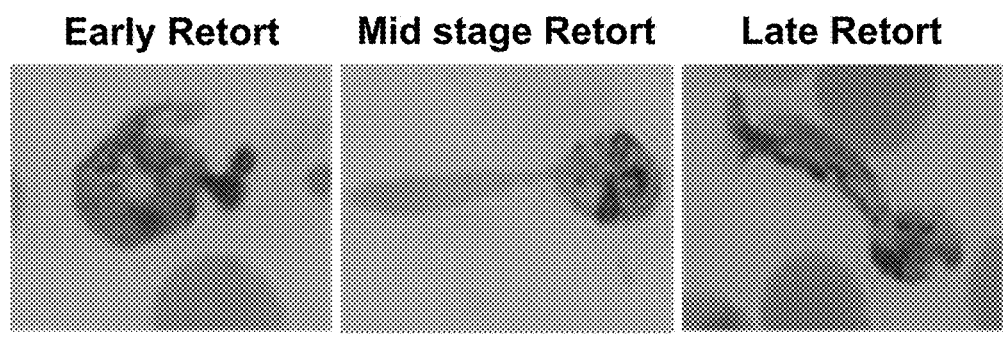
FIGS. 2A-2B provide sample images of post-zygote stage development of *Plasmodium falciparum* produced in vitro.
Figure 2B:
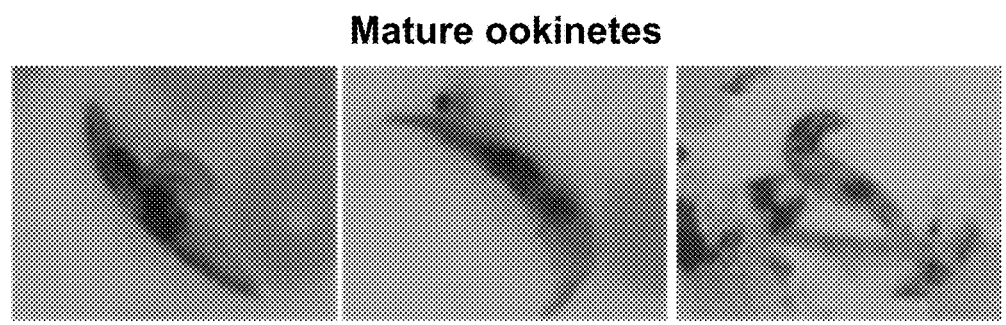
Figures 3A, 3B:
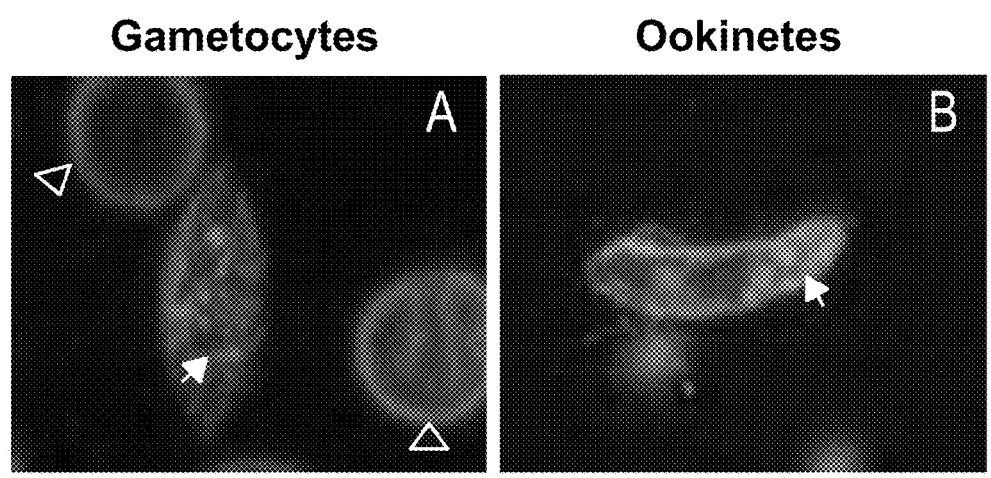
FIGS. 3A-3B show immunostaining of gametocytes (FIG. 3A) and ookinetes (FIG. 3B) using antibodies against Glycophorin A and Pfs25. Antibodies against Glycophorin A (open arrows point to red staining) and Pfs25 (closed arrows point to green staining).

Optimizing Methods for Reproducibly Producing and Purifying Large Numbers of *P. falciparum* Ookinetes In Vitro Ookinete production from gametocyte cultures of different ages, and at high and low gametocyte densities was assessed. Ookinetes and late retorts were reproducibly produced (FIGS. 2A-2B) from both high- and low-density cultures 14-22 days post gametocyte induction (Table 1). Retorts are intermediate forms of the parasite during its development from zygote to ookinete and both ookinetes and late retorts (FIGS. 2A-2B) transform to oocysts in mosquitoes. Parasites were taken from a gametocyte culture 18 days post induction. Early retorts (FIG. 2A) were first seen ~14 h and ookinetes from 24 h after initiation of the ookinete culture. Giemsa-stained smears of cultures examined by light microscopy showed a mixture of round macrogametes and zygotes, as well as crescent-shaped gametocytes and ookinetes in the cultures. Zygotes were distinguished from macrogametes by the presence of a prominent nucleus. Ookinetes were distinguished from gametocytes by the presence of prominent nuclei and lack of a surrounding erythrocyte membrane. Two other approaches were used to provide estimates of conversion and purification rates. First, monoclonal antibodies (mAbs) directed against molecules expressed on different stages of the parasite were screened: Pfs 48/45 expressed on mature macrogametocytes and macrogametes, Pfs 230 on macrogametes and zygotes, Pfs25 on gametes and ookinetes, and PfCelTOS on ookinetes and PfSPZ (data not shown). Pfs230 localized on gametocytes and macrogametes, while Pfs48/45 localized to gametes and retorts. Pfs25 variably localized to gametocytes, but was strongly expressed on retorts and ookinetes. By labeling cultured parasites with antibodies against Pfs25 (closed arrows point to green staining) and the erythrocyte antigen, Glycophorin A (open arrows point to red staining) (FIGS. 3A-3B), gametocytes were distinguished from ookinetes based on presence or absence of an erythrocyte membrane, respectively.

Several approaches were taken to purify and enrich cultured ookinetes away from uninfected erythrocytes. Approximately 90% of uninfected erythrocytes could be removed using Lympholyte-H gradient centrifugation, but the ookinetes co-purified with gametocytes, gametes and zygotes. A 3-step procedure was developed to purify and enrich. This procedure was successful and achieved >70% enrichment. The mean efficiency of transformation of stage V gametocytes to ookinetes in vitro was 13% (range=8-21%, Table 1).

TABLE 1

Summary of *Plasmodium falciparum* in vitro ookinete cultures.

| | Total number | | Transformation efficiency |
|---|---|---|---|
| Exp. # | Stage V gametocytes | Ookinetes and late retorts | of gametocytes to ookinetes and late retorts |
| 1 | $8.25 \times 10^7$ | $1.06 \times 10^7$ | 13% |
| 2 | $8.94 \times 10^7$ | $9.72 \times 10^6$ | 11% |
| 3 | $7.29 \times 10^7$ | $5.85 \times 10^6$ | 8% |
| 4 | $7.61 \times 10^7$ | $1.63 \times 10^7$ | 21% |
| 5 | $1.03 \times 10^8$ | $8.54 \times 10^6$ | 8% |
| 6 | $1.02 \times 10^8$ | $1.80 \times 10^7$ | 18% |
| Mean | | | 13% |

Gametocyte cultures had from 2.1% to 4.6% stage V gametocytes and stage V gametocytes from days 14 to 22 post gametocyte induction were used to produce ookinetes in vitro. Ookinetes ranged from 8.0% to 21.0% of the total number of stage V gametocytes added to the culture.

Example 2

Production of *P. falciparum* Sporozoites from Ookinetes In Vitro

Figure 4:
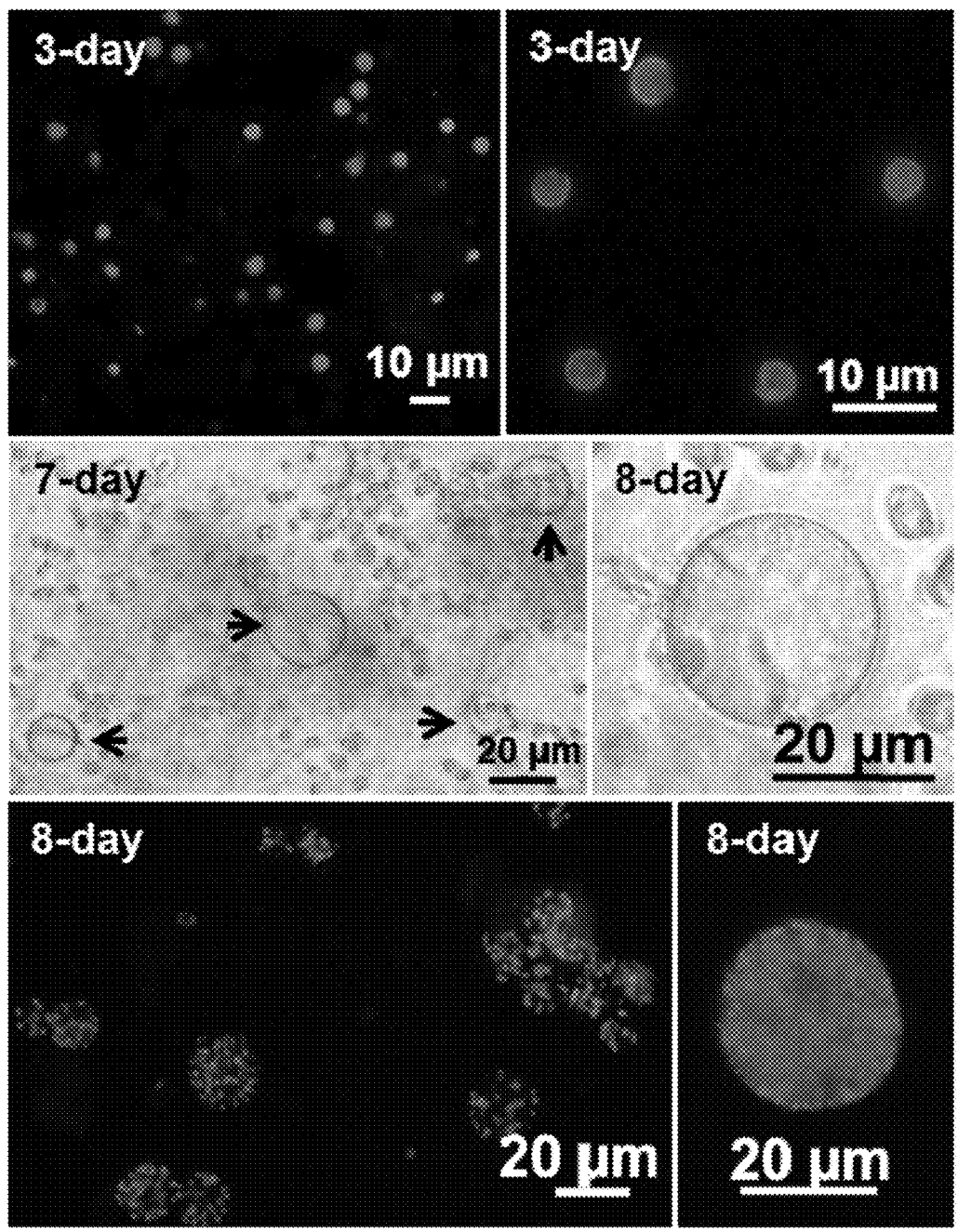
FIG. 4 shows IFA and bright field images of Pf oocysts developing in vitro. 3 day (upper panel) and 8 day (lower panel) oocysts detected by IFA using anti-Pfs25 and anti-PfCSP mAbs are shown. 8 day cultures were permeabilized for IFA. Punctated staining in 8-day oocysts suggests budding Pf SPZ. Middle panel shows 7 to 8 day oocysts developing in culture. Arrows indicate oocysts.

The first step was to efficiently produce oocysts. Briefly, stage V gametocytes from in vitro cultures were transferred into an exflagellation medium (FBS, 0.1% glucose, 0.1% sodium bicarbonate, and 0.022% xanthurenic acid), and after incubation the zygotes were transferred into a modified ookinete medium (20% FBS, RPMI medium, 0.25% trehalose, 0.25% dextrose, 0.04% sodium bicarbonate, 10 units/mL penicillin and 10 µg/mL streptomycin) and layered onto modified Matrigel-coated 8-well slides. To coat the 8-well slides, Matrigel was diluted with RPMI medium and poured into 8-well slides. These slides were incubated at 37° C. for 2 h and excess medium was removed. The Matrigel coated slides were further modified by seeding *Drosophila* Schneider S2 cells on top of the Matrigel before layering zygotes. Differentiated ookinetes invaded into the Matrigel. Undifferentiated zygotes and ookinetes that did not invade into the Matrigel were washed off during the change from ookinete to oocyst medium (Schneider's *Drosophila* medium, 20% FBS, 0.04% sodium bicarbonate, 0.25% trehalose, 50 µg/mL hypoxanthine, 0.1M HEPES, essential amino acids (1×, GIBCO), 0.04 µg/mL para-aminobenzoic acid (PABA), 10 units/mL penicillin and 10 µg/mL streptomycin, 1.5% lipoproteins, 0.1% cholesterol, and vitamins (1×, GIBCO)) 24 h after incubation. In both ookinete and oocyst medium, S2 cells were added (FIG. 4). Three-day (FIG. 4, upper panel) and 8-day (FIG. 4, lower panel) oocysts detected by IFA using anti-Pfs25 and anti-Pf CSP mAbs are shown. Eight-day cultures were permeabilized for IFA. Punctated staining in 8-day oocysts suggested budding PfSPZ. In the middle panel (FIG. 4) arrows indicate 7 to 8-day oocysts developing in culture. After initial experiments, culture conditions, such as the concentration of the Matrigel used for coating and the number of zygotes seeded to each well, were modified to significantly increase transformation efficiency of development from stage V gametocytes to 8 day oocysts. Using this modified in vitro culture protocol, 2.4 to 12.5% (mean 8.3%) transformation of stage V gametocyte to 8 day oocysts was consistently achieved (Table 2). This was a major improvement upon the 0.13% recorded initially before the modification of the in vitro culture protocol. The transformation efficiency in mosquitoes from stage V gametocytes to oocysts was 0.22% in 74 independent membrane feeding assays conducted at Sanaria (Li et al. in prep.). This transformation efficiency was comparable to that reported in the literature [22, 23]. The 8.3% transformation efficiency in vitro was 39-fold higher than that observed in mosquitoes (Tables 2, 3). The size and structure of oocysts developing in vitro (FIGS. 4, 5A, 8A-C) and in mosquitoes (FIG. 5B) were similar. FIG. 5A shows IFA of in vitro-cultured 7-day oocysts stained with ant-PfCSP mAb and Mercurochrome stained mosquito midgut 7-day oocysts (FIG. 5B).

In vitro cultures were harvested on day 15 and/or day 18 by collecting the culture supernatant from the wells including unattached S2 cells. The numbers of morphologically developed PfSPZ were counted in a cellometer and an aliquot was stained using fluorescent anti-PfCSP mAb for confirmation (FIG. 6B, Table 4). Pf SPZ developed in culture well were detected after fixation of the well staining with fluorescent anti-Pf CSP mAb (FIG. 6A). In 7 independent experiments, between 180,000 and 350,000 mature Pf SPZ/harvest from ten 8-well slides were produced. In all experiments, two morphologically different forms of Pf SPZ were present. Morphologically mature Pf SPZ looked identical to salivary gland Pf SPZ, were motile, 10-13 µm long, and highly reactive to anti-Pf CSP mAb (FIGS. 6A-B, Table 4). Short form, immature Pf SPZ were <10 µm long, but still motile and highly reactive to anti-Pf CSP mAb. In all the experiments reported, only morphologically mature Pf SPZ were quantified. Harvesting on both 15 and 18 days from the same cultures increased yields to ~500,000 PfSPZ per ten slides.

Figure 7:
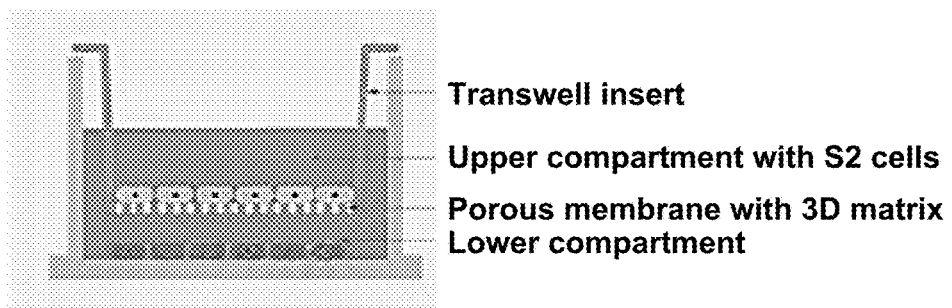
FIG. 7 illustrates an example of an in vitro 3D culture system.
Figures 8A, 8B, 8C:
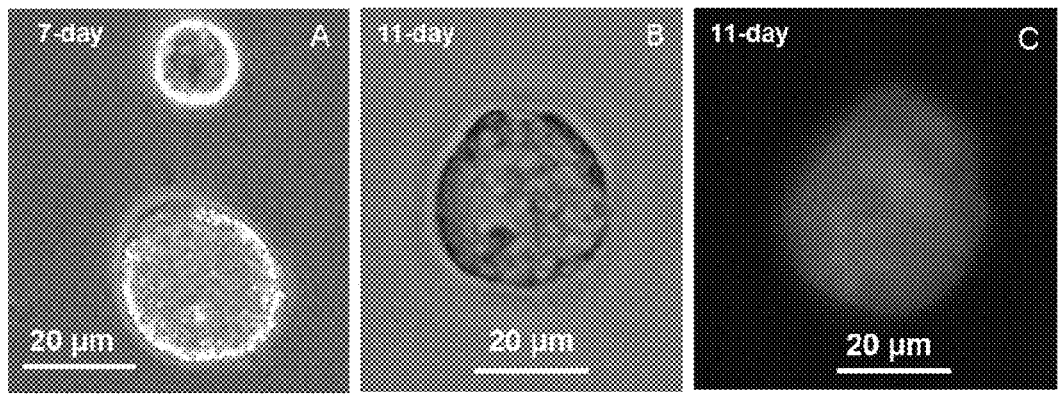
FIGS. 8A-8C show sample images of oocysts from transwell insert modified 3D matrix extracted by centrifugation.

Subsequently, a 3D transwell system was tested. In two independent culture experiments using this approach, 228,000 and 208,000 morphologically mature Pf SPZs were harvested from one 6-well plate culture. Initially, two commercially available 3D matrices that were found to be suitable for in vitro culture of oocysts were used. The 3D Life Hydrogel (Cellendes GmbH, Germany) is used to culture cells in a biomimetic 3D environment, and the AlgiMatrix™ 3D Culture System (Gibco/Invitrogen) is an animal origin-free bioscaffold that facilitates 3D cell culture. Both support Pf sporogony. 3D Life Hydrogel required galactosidase digestion for releasing Pf SPZ from the matrix while mature Pf SPZ were trapped in the Algimatrix matrix. Therefore, we developed a transwell insert based culture system in conjunction with Alvetex 3D culture technology (AMS Biotechnology (Europe) Limited, UK) as an alternative. Transwell inserts allowed two-compartment culturing once they were inserted into plate wells (FIG. 7). In this system, an inert 200 µm thick porous polystyrene scaffold coated with Matrigel was placed on the insert's porous membrane. Zygotes seeded onto this 3D matrix differentiated to ookinetes, invaded the Matrigel coated polystyrene scaffold and transformed to oocysts. The upper compartment was seeded with S2 cells. Oocysts developed in this matrix and PfSPZ were released into and collected from the lower compartments. In preliminary experiments, this system supported Pf sporogonic development (Table 5), and oocyst development and retention were very similar to chamber slide cultures (Tables 2, 3). To assess sporogonic development, the porous membrane along with the matrix was removed and oocysts were collected by centrifugation. Transformation efficiency from stage V gametocytes to 7- and 11-day oocysts (FIGS. 8A-C) was 10.3% (range 9-11.5) and 9.0% (range 7.8-10.7), respectively (Table 5). The number of 11-day oocysts represented a tremendous increase, and indicated significant retention of oocysts during culture. Furthermore, extracted oocysts were similar in appearance to oocysts that developed in mosquito midguts at 11 days and these in vitro formed oocysts expressed PfCSP (FIG. 8C). FIGS. 8A-B shows phase contrast images of oocysts in a cellometer used for quantification (FIGS. 8A & B), and IFA of extracted oocysts in suspension (not permeabilized) using fluorescently labeled anti-Pf CSP mAb (FIG. 8C). Staining of oocysts was carried out in suspension without permeabilization, and therefore, PfCSP-stained oocysts had a uniform rather punctated pattern of PfCSP expression (FIG. 8C).

In two independent culture experiments, 228,000 and 208,000 morphologically developed PfSPZs were harvested from one 6-well plate culture using 6 modified inserts. This was a minimally 3-fold increase in yield compared to the numbers achieved with the 8-well slides (Tables 4, 5). In particular, Table 4 shows results of 8-well culture where as Table 5 shows results of transwell culture. This transwell insert culture condition offered several advantages as it: i) reduced the loss of Matrigel during media changes, ii) permitted repeat harvesting of PfSPZ from a single culture, iii) was amenable to coating the matrix with different extracellular matrix proteins, such as laminins and collagens, and iv) was suitable for scale up and automation using a suitable liquid handling system.

This result represents minimally a 3-fold increase in the numbers of mature Pf SPZ harvested from oocysts as compared to previous experiments.

TABLE 2

Transformation efficiency of gametocyte to 3 day and 7 to 8 day oocysts in in vitro culture using 8-well chamber slides.

| Exp. # | Stage V gametocytes/ well | Geometric mean # of 3 day oocysts/ well (range) | Transformation efficiency to 3 day oocysts | Geometric mean # 7 to 8 day oocysts/ well (range) | Transformation efficiency of gametocytes to 8 day oocysts | Mean transformation efficiency to 8 day oocysts |
|---|---|---|---|---|---|---|
| 1 | 15,000 | 428 (180-540) | 2.9% | 359 (260-375) | 2.4% | 8.9% |
| 2 | 15,000 | 2113 (1790-2695) | 14.1% | 1877 (1470-2585) | 12.5% | |
| 3 | 15,000 | 2334 (2235-2405) | 15.5% | 1786 (1450-2220) | 11.9% | |
| 1 | 25,000 | 1107 (650-1685) | 4.4% | 978 (900-1050) | 3.9% | 8.4% |
| 2 | 25,000 | 2916 (1635-4515) | 11.8% | 2210 (1970-2825) | 8.8% | |
| 3 | 25,000 | 3888 (3730-4070) | 15.5% | 3092 (2885-3365) | 12.4% | |
| 1 | 50,000 | 2367 (2110-2995) | 4.8% | 1846 (1810-1910) | 3.7% | 7.5% |
| 2 | 50,000 | 5695 (3765-7860) | 11.4% | 3931 (3475-4250) | 7.9% | |

TABLE 2-continued

Transformation efficiency of gametocyte to 3 day and 7 to 8
day oocysts in in vitro culture using 8-well chamber slides.

| Exp. # | Stage V gametocytes/ well | Geometric mean # of 3 day oocysts/ well (range) | Transformation efficiency to 3 day oocysts | Geometric mean # 7 to 8 day oocysts/ well (range) | Transformation efficiency of gametocytes to 8 day oocysts | Mean transformation efficiency to 8 day oocysts |
|---|---|---|---|---|---|---|
| 3 | 50,000 | 6997 (5650-9150) | 14.0% | 5407 (3835-6595) | 10.8% | |

3 day and 8 day oocysts were estimated by IFA using anti-Pfs25 and anti-Pf CSP mAbs respectively. Oocysts from triplicate wells were counted and the geometric mean oocysts/well calculated. Transformation efficiency was the percentage of stage V gametocytes that developed into oocysts. For each experiment the same gametocyte culture seeded at 15,000-50,000 gametocytes/well was used.

TABLE 3

Efficiency of gametocyte conversion to 7 or
8 day oocysts in mosquitoes and in vitro.

|  | Mosquitoes | In vitro |
|---|---|---|
| Mean (±SD) # of gametocytes | 21,781 ± 3,581[a] | 25,000[b] |
| Mean (±SD) # of oocysts | 47.2 ± 32.9[c] | 2093.4 ± 1061.8[d] |
| Conversion rate | 0.22% | 8.37% |

[a]Estimated gametocytes ingested per mosquito.
[b]Number per well (N = 3) per experiment.
[c]Mean per mosquito midgut is the mean of the geometric mean of 74 independent SMFAs and N = 20-25 for each experiment (Li et al. in preparation)
[d]Mean per well is the mean of the geometric means of 3 independent experiments.

Example 3

Figure 9A:
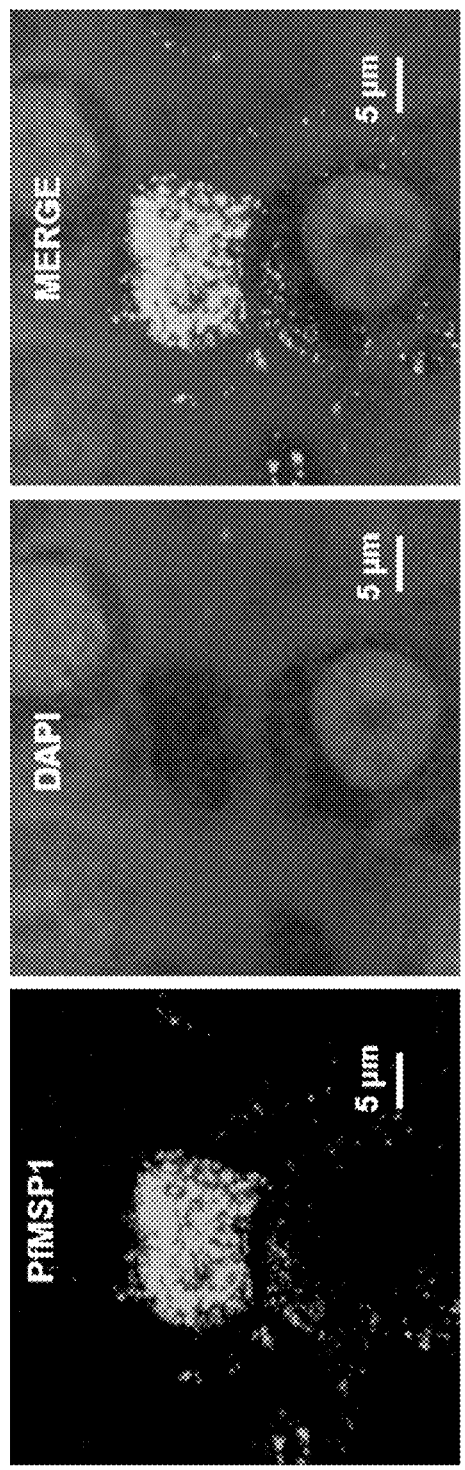
FIGS. 9A-9B show development of in vitro-produced and mosquito produced Pf SPZ in HC-04 cells. Confocal micrographs of 6 day liver stages in HC-04 cells following infection with in vitro-produced Pf SPZ (FIG. 9A, top panels) or mosquito-produced, aseptic, purified, cryopreserved Pf SPZ (FIG. 9B, bottom panels).
Figure 9B:
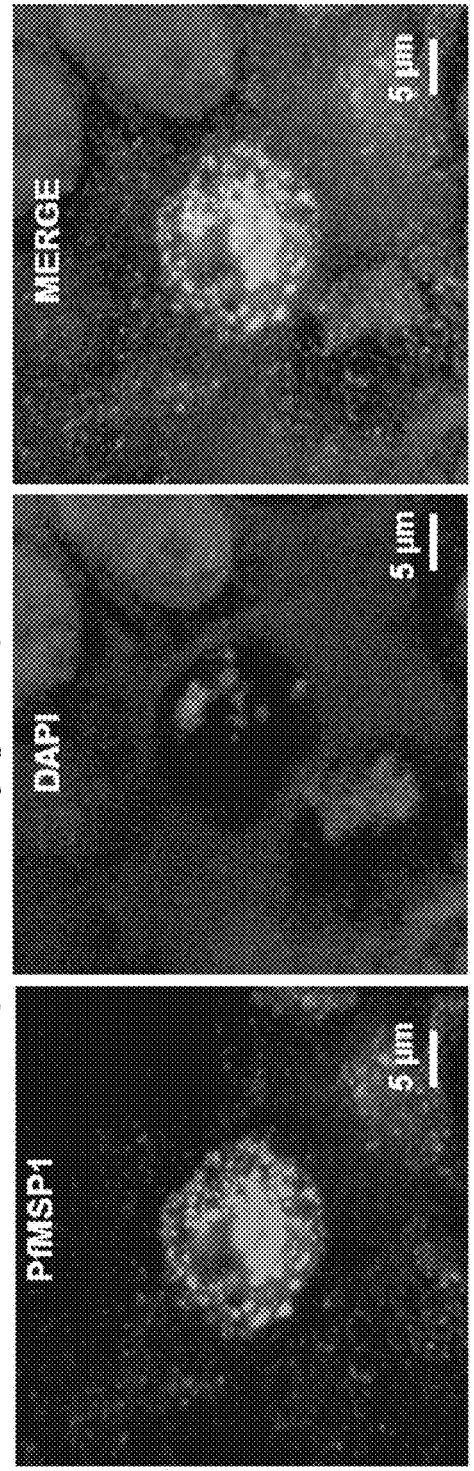

Demonstration that In Vitro-Reared *P. falciparum* Sporozoites and *P. falciparum* Sporozoites Ontogenically Developed in *Anopheles stephensi* Mosquitoes Each Invade and Develop within a Human Hepatocyte Cell Line (HC-04) with Similar Efficiencies In vitro-reared Pf SPZ were tested for their infectivity in a 6-day hepatocyte assay, which is used routinely to assess potency. The assay is typically carried out with Pf SPZ before and after cryopreservation. Fresh and cryopreserved Pf SPZ produce 6-day liver stage parasites that are morphologically identical, but there is a 5-25% loss of potency due to cryopreservation [5]. The in vitro-reared Pf SPZ are more akin to fresh mosquito-derived PfSPZ, therefore comparisons were made with readouts from fresh PfSPZ generated during manufacturing campaigns. In 7 consecutive production campaigns, 20.7-32.7 mature 6-day parasites expressing Pf MSP-1 developed from 50,000 mosquito-produced fresh Pf SPZ (Table 4). In vitro-reared PfSPZ were inoculated into 3 wells plated with HC-04 cells (a human hepatocyte cell line shown to support infection of Pf SPZ produced in vivo) [24, 25] and incubated for 6-days (FIG. 9A upper panels, Table 4). FIGS. 9A-9B shows confocal micrographs of 6 day liver stages in HC-04 cells following infection with in vitro-reared Pf SPZ (FIG. 9A upper panels) or mosquito-produced, aseptic, purified, cryopreserved Pf SPZ (FIG. 9B lower panels). In 4 independent 6-day hepatocyte assays, in vitro-produced Pf SPZ seeded at 56,598±7,294 Pf SPZ/well produced 28.6±7.0 Pf MSP1-expressing 6-day parasites (Table 4). This was comparable to the 25.7±4.1 Pf MSP1-expressing parasites seen with fresh, aseptic, purified Pf SPZ in this assay (Table 4) and slightly more than with cryopreserved Pf SPZ (data not shown). These data also suggested that 18-day in vitro-produced Pf SPZ were more infectious than 15 day in vitro-reared Pf SPZ. The size of the 6-day parasites developed in HC-04 cells from in vitro- and in vivo (mosquito)-produced Pf SPZ were similar (FIGS. 9A-9B). As a positive control for the photomicrographs, aseptic, purified, cryopreserved Pf SPZ from mosquito salivary glands were incubated in HC-04 cells and assessed for Pf MSP1 expression (FIG. 9B). These data demonstrated that the in vitro-produced Pf SPZ were as infectious in hepatocyte cultures as fresh mosquito-produced Pf SPZ.

TABLE 4

In vitro Pf SPZ production and comparative infectivity in vitro-harvested and fresh,
aseptic, purified salivary gland-derived Pf SPZ in a 6-day hepatocyte assay.

In vitro cultures were harvested on days 15 and/or 18 post culture initiation.
No. of morphologically mature PfSPZ harvested was determined by counting on a cellometer. Immature forms were not counted. The infectivity of the Pf SPZs was determined by counting the numbers of Pf MSP1-expressing parasites by IFA in Sanaria's 6-day hepatocyte assay in HC04 cells.

Infectivity of fresh, aseptic, purified, salivary gland-derived Pf SPZ produced in 7 consecutive GMP manufacturing campaigns (50,000 PfSPZ/well).

| | Numbers of morphologically mature Pf SPZ harvested on days 15 and 18. | | Hepatocyte assay | | | | | |
|---|---|---|---|---|---|---|---|---|
| | | | Number Pf SPZ seeded/well | | Mean number 6-day parasites/well ± SD | | | Mean number of 6-day parasites/well ± SD |
| Exp. # | 15 day | 18 day | 15 day | 18 day | 15 day | 18 day | Campaign | |
| 1 | 203,125 | 247,000 | 60,937 | 71,500 | 24.5 ± 6.8 | 32.3 ± 5.6 | 1 | 20.7 ± 3.5 |
| 2 | 180,500 | ND | 47,500 | ND | 21.7 ± 2.1 | ND | 2 | 32.7 ± 1.5 |
| 3 | 200,000 | 231,000 | 50,000 | 55,000 | 17 ± 2.3 | 37 ± 5.0 | 3 | 21.3 ± 4.0 |

TABLE 4-continued

In vitro Pf SPZ production and comparative infectivity in vitro-harvested and fresh, aseptic, purified salivary gland-derived Pf SPZ in a 6-day hepatocyte assay.

In vitro cultures were harvested on days 15 and/or 18 post culture initiation. No. of morphologically mature PfSPZ harvested was determined by counting on a cellometer. Immature forms were not counted. The infectivity of the Pf SPZs was determined by counting the numbers of Pf MSP1-expressing parasites by IFA in Sanaria's 6-day hepatocyte assay in HC04 cells.

Infectivity of fresh, aseptic, purified, salivary gland-derived Pf SPZ produced in 7 consecutive GMP manufacturing campaigns (50,000 PfSPZ/well).

| | Numbers of morphologically mature Pf SPZ harvested on days 15 and 18. | | Hepatocyte assay | | | | | |
|---|---|---|---|---|---|---|---|---|
| | | | Number Pf SPZ seeded/well | | Mean number 6-day parasites/well ± SD | | Manufacturing Campaign | Mean number of 6-day parasites/well ± SD |
| Exp. # | 15 day | 18 day | 15 day | 18 day | 15 day | 18 day | | |
| 4 | 204,000 | 258,750 | 55,000 | 56,250 | 32.3 ± 3.8 | 35.3 ± 0.9 | 4 | 28.3 ± 1.5 |
| 5 | 350,000 | ND | ND | ND | ND | ND | 5 | 23.0 ± 2.6 |
| 6 | 217,000 | 253,750 | ND | ND | ND | ND | 6 | 29.0 ± 2.6 |
| 7 | 210,000 | 280,500 | ND | ND | ND | ND | 7 | 25.0 ± 1.7 |
| Mean ± SD | | | 56,598 ± 7,294 | | 28.6 ± 7.0 | | N/A | 25.7 ± 4.1 |

ND; not determined.
6-day hepatocyte assays are ongoing.

TABLE 5

Transformation efficiency of stage V gametocytes to 7 and 11-day oocysts using 3D culture transwell inserts and polystyrene matrix coated with Matrigel.

| Number of stage V gametocytes/insert | Number of oocysts/insert | | Transformation efficiency: stage V gametocytes to oocysts | |
|---|---|---|---|---|
| | 7 day | 11 day | 7 day | 11 day |
| 250,000 | 28,690 | 26,400 | 11.5% | 10.7% |
| 300,000 | 31,300 | 25,800 | 10.4% | 8.6% |
| 274,000 | 24,600 | 21,400 | 9.0% | 7.8% |

Oocysts were extracted from the matrix by centrifugation and counted on a cellometer.

These results show methods for producing Pf oocysts in vitro with an efficiency 39 times greater than oocysts produced in mosquitoes. The in vitro-reared Pf SPZ invaded and developed to mature 6 day liver stage schizonts expressing Pf merozoite surface protein 1 with at least as good efficiency as Pf SPZ freshly dissected from mosquitoes.

In the foregoing, the present invention has been described with reference to suitable embodiments, but these embodiments are only for purposes of understanding the invention and various alterations or modifications are possible.

REFERENCES

1. Sachs J, and Malaney P. The economic and social burden of malaria. *Nature* 415: 680-685, 2002.
2. Murray C J, et al. Global malaria mortality between 1980 and 2010: a systematic analysis. *Lancet* 379: 413-431, 2012.
3. World Health Organization. Global Malaria Programme. *World Malaria Report* 2013: World Health Organization 2013.
4. Health Protection Agency (HPA) UK Press Release. 25 Apr. 2011. Malaria cases up almost 30 per cent in two years as it's revealed most cases haven't taken antimalaria tablets.
5. Mali S, Kachur S P, and Arguin P M. Malaria surveillance—United States, 2010. *MMWR Surveill Summ* 61: 1-17, 2012.
6. Cullen K A, Arguin P M, and Division of Parasitic D M, Center for Global Health C. D. C., Malaria surveillance—United States, 2011. *MMWR Surveill Summ* 62 Suppl 5: 1-17, 2013.
7. Beadle C, and Hoffman S L. History of malaria in the United States Naval Forces at war: World War I through the Vietnam conflict. *Clin Infect Dis* 16: 320-329, 1993.
8. Alonso P L, et al. A research agenda for malaria eradication: vaccines. *PLoS Med* 8: e1000398, 2011.
9. Kester K E, et al. Randomized, double-blind, phase 2a trial of *falciparum* malaria vaccines RTS,S/AS01B and RTS,S/ASO2A in malaria-naive adults: safety, efficacy, and immunologic associates of protection. *J Infect Dis* 200: 337-346, 2009.
10. Agnandji S T, et al. First results of phase 3 trial of RTS,S/AS01 malaria vaccine in African children. *N Engl J Med* 365: 1863-1875, 2011.
11. Agnandji S, et al. A phase 3 trial of RTS,S/AS01 malaria vaccine in African infants. *N Engl J Med* 367: 2284-2295, 2012.
12. Olotu A, et al. Four-year efficacy of RTS,S/AS01E and its interaction with malaria exposure. *N Engl J Med* 368: 1111-1120, 2013.
13. Seder R A, et al. Protection against malaria by intravenous immunization with a nonreplicating sporozoite vaccine. *Science* 341: 1359-1365, 2013.
14. Mutapi F, Billingsley P F, Secor W E. Infection and treatment immunizations for successful parasite vaccines. *Trends Parasitol*. 2013 March; 29(3):135-41.
15. Roestenberg M, et al. Controlled Human Malaria Infections by Intradermal Injection of Cryopreserved *Plasmodium falciparum* Sporozoites. *Am J Trop Med Hyg* 88: 5-13, 2013.
16. Sheehy S H, et al. Optimising Controlled Human Malaria Infection Studies Using Cryopreserved Parasites Administered by Needle and Syringe. *PLoS One* 8: e65960, 2013.
17. Hoffman S L, et al. Development of a metabolically active, non-replicating sporozoite vaccine to prevent *Plasmodium falciparum* malaria. *Hum Vaccin* 6: 97-106, 2010.

18. Trager W, and Jensen J B. Human malaria parasites in continuous culture. *Science* 193: 673-675, 1976.
19. Warburg A, and Miller L H. Sporogonic development of a malaria parasite in vitro. *Science* 255: 448-450, 1992.
20. Warburg A, and Schneider I. In vitro culture of the mosquito stages of *Plasmodium falciparum*. *Exp Parasitol* 76: 121-126, 1993.
21. Al-Olayan E M, Beetsma A L, Butcher G A, Sinden R E, and Hurd H. Complete development of mosquito phases of the malaria parasite in vitro. *Science* 295: 677-679, 2002.
22. Vaughan J A, Noden B H, and Beier J C. Sporogonic development of cultured *Plasmodium falciparum* in six species of laboratory-reared *Anopheles* mosquitoes. *Am J Trop Med Hyg* 51: 233-243, 1994.
23. Pradel G. Proteins of the malaria parasite sexual stages: expression, function and potential for transmission blocking strategies. *Parasitology* 134: 1911-1929, 2007.
24. Prachumsri, J. & N. Yimamnuaychok, U.S. Pat. No. 7,015,036, Mar. 21, 2006.
25. Sattabongkot J, Yimamnuaychoke N, Leelaudomlipi S, Rasameesoraj M, Jenwithisuk R, Coleman R E, Udomsangpetch R, Cui L, Brewer T G. (2006) Establishment of a human hepatocyte line that supports in vitro development of the exo-erythrocytic stages of the malaria parasites *Plasmodium falciparum* and *P. vivax*. Am J Trop Med Hyg. 74(5):708-15, 2006.
26. Schneider I. (1972) Cell lines derived from late embryonic stages of *Drosophila melanogaster*. J Embryol Exp Morphol. 1972 April; 27(2):353-65.
27. Hughes, C. S., Postovit, L. M., Lajoie, G. A. (2010). "Matrigel: a complex protein mixture required for optimal growth of cell culture". Proteomics 10 (9): 1886-90.
28. Benton, G., George, J., Kleinman, H. K., Arnaoutova, I. (2009). "Advancing science and technology via 3D culture on basement membrane matrix". Journal of cellular physiology 221 (1): 18-25.

What is claimed is:

1. A composition comprising (i) in vitro-reared infectious *Plasmodium* sporozoites of human host range absent any mosquito material, wherein sporogony from gametocyte stage to mature sporozoite stage is external to mosquitoes, and (ii) an excipient, diluent, or carrier.

2. The composition of claim 1, wherein the in vitro-reared infectious *Plasmodium* sporozoites of human host range are at least 90% as infectious to human hepatocytes as *Plasmodium* sporozoites of human host range reared in a mosquito.

3. The composition of claim 1, wherein the in vitro-reared infectious *Plasmodium* sporozoites of human host range are aseptic.

4. The composition of claim 1, wherein the species of said in vitro-reared infectious *Plasmodium* sporozoites of human host range is *P. falciparum*.

5. A vaccine composition comprising (a) aseptic in vitro-reared infectious *Plasmodium* sporozoites of human host range absent any mosquito material and (b) a pharmaceutically acceptable diluent.

6. A method of inducing an immune response in a human subject against *Plasmodium*-specific antigens comprising administering to said human subject a composition comprising aseptic in vitro-reared infectious *Plasmodium* sporozoites of human host range and a pharmaceutically acceptable diluent.

7. The vaccine composition of claim 5, wherein the aseptic in vitro-reared infectious *Plasmodium* sporozoites of human host range are attenuated.

8. The vaccine composition of claim 5, wherein the aseptic in vitro-reared infectious *Plasmodium* sporozoites of human host range are not attenuated.

9. The method of claim 6, wherein the aseptic in vitro-reared infectious *Plasmodium* sporozoites of human host range are attenuated.

10. The method of claim 6, wherein the aseptic in vitro-reared infectious *Plasmodium* sporozoites of human host range are not attenuated and the human subject is further administered an anti-malarial agent.

11. In vitro-reared infectious *Plasmodium* sporozoites of human host range, wherein sporogony from gametocyte stage to mature sporozoite stage is external to mosquitoes, and wherein the in vitro-reared infectious *Plasmodium* sporozoites of human host range are attenuated.

12. The attenuated in vitro-reared infectious *Plasmodium* sporozoites of human host range of claim 11, which are absent any mosquito material.

13. The attenuated in vitro-reared infectious *Plasmodium* sporozoites of human host range of claim 11, which are at least 90% as infectious to human hepatocytes as *Plasmodium* sporozoites of human host range reared in a mosquito.

14. The attenuated in vitro-reared infectious *Plasmodium* sporozoites of human host range of claim 11, which are aseptic.

15. The attenuated in vitro-reared infectious *Plasmodium* sporozoites of human host range of claim 11, wherein the species of said *Plasmodium* sporozoites is *P. falciparum*.

16. The method of claim 6, wherein the aseptic in vitro-reared infectious *Plasmodium* sporozoites of human host range are absent any mosquito material.

17. The method of claim 6, wherein the aseptic in vitro-reared infectious *Plasmodium* sporozoites of human host range are at least 90% as infectious to human hepatocytes as *Plasmodium* sporozoites of human host range reared in a mosquito.

18. The method of claim 6, wherein the species of said aseptic in vitro-reared infectious *Plasmodium* sporozoites of human host range is *P. falciparum*.

* * * * *